United States Patent
Erickstad et al.

(10) Patent No.: US 11,041,199 B2
(45) Date of Patent: Jun. 22, 2021

(54) TEMPERATURE CONTROL FOR ANALYSIS OF NUCLEIC ACIDS AND OTHER ANALYTES

(71) Applicant: OMNIOME, INC., San Diego, CA (US)

(72) Inventors: Michael John Erickstad, San Diego, CA (US); Eric Villarreal, Cardiff by the Sea, CA (US); Vyshnavi Balakrishnan, San Diego, CA (US); Xenia Aparicio, Escondido, CA (US); Rebecca McGinley, San Diego, CA (US); Arnold Oliphant, Morgan Hill, CA (US)

(73) Assignee: Omniome, Inc., San Diego, CA (US)

( * ) Notice: Subject to any disclaimer, the term of this patent is extended or adjusted under 35 U.S.C. 154(b) by 0 days.

(21) Appl. No.: 16/721,771

(22) Filed: Dec. 19, 2019

(65) Prior Publication Data
US 2020/0199667 A1    Jun. 25, 2020

Related U.S. Application Data

(60) Provisional application No. 62/782,565, filed on Dec. 20, 2018.

(51) Int. Cl.
*C12Q 1/6869* (2018.01)
*B01L 3/00* (2006.01)
*B01L 7/00* (2006.01)

(52) U.S. Cl.
CPC ...... *C12Q 1/6869* (2013.01); *B01L 3/502715* (2013.01); *B01L 7/52* (2013.01); *B01L 2300/0877* (2013.01); *B01L 2300/1822* (2013.01)

(58) Field of Classification Search
CPC .......... C12Q 1/6869; B01L 3/502715
See application file for complete search history.

(56) References Cited

U.S. PATENT DOCUMENTS

| | | |
|---|---|---|
| 5,599,675 A | 2/1997 | Brenner et al. |
| 5,695,934 A | 12/1997 | Brenner |
| 5,750,341 A | 5/1998 | Macevicz |
| 5,863,722 A | 1/1999 | Brenner |
| 5,888,737 A | 3/1999 | DuBridge et al. |
| 6,140,489 A | 10/2000 | Brenner |
| 6,175,002 B1 | 1/2001 | DuBridge et al. |
| 6,210,891 B1 | 4/2001 | Nyren et al. |
| 6,258,568 B1 | 7/2001 | Nyren |
| 6,266,459 B1 | 7/2001 | Walt et al. |
| 6,274,320 B1 | 8/2001 | Rothberg et al. |
| 6,355,431 B1 | 3/2002 | Chee et al. |
| 6,770,441 B2 | 8/2004 | Dickinson et al. |
| 6,859,570 B2 | 2/2005 | Walt et al. |
| 7,057,026 B2 | 6/2006 | Barnes et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,329,860 B2 | 2/2008 | Feng et al. |
| 7,405,281 B2 | 7/2008 | Xu et al. |
| 7,482,120 B2 | 1/2009 | Buzby |
| 7,544,794 B1 | 6/2009 | Benner |
| 7,622,294 B2 | 11/2009 | Walt et al. |
| 7,956,171 B2 | 6/2011 | Siddiqi |
| 8,034,923 B1 | 10/2011 | Benner et al. |
| 8,071,755 B2 | 12/2011 | Efcavitch et al. |
| 8,252,911 B2 | 8/2012 | Bjornson et al. |
| 8,530,164 B2 | 9/2013 | Patel et al. |
| 8,808,989 B1 | 8/2014 | Efcavitch et al. |
| 8,914,241 B2 * | 12/2014 | Kain .............. G16B 30/00 702/20 |
| 9,399,798 B2 | 7/2016 | Stupi et al. |
| 9,951,385 B1 | 4/2018 | Vijayan et al. |
| 10,077,470 B2 | 9/2018 | Vijayan et al. |
| 10,173,148 B2 | 1/2019 | Waldbaur et al. |
| 10,365,256 B2 | 7/2019 | Guzzonato et al. |
| 10,401,331 B2 | 9/2019 | Dryden et al. |
| 10,443,098 B2 | 10/2019 | Vijayan et al. |
| 10,501,796 B2 | 12/2019 | Buermann et al. |
| 10,578,578 B2 * | 3/2020 | Rearick ............. G05D 23/1931 |

(Continued)

FOREIGN PATENT DOCUMENTS

| | | |
|---|---|---|
| EP | 1959255 A2 | 8/2008 |
| WO | 91/06678 | 5/1991 |

(Continued)

OTHER PUBLICATIONS

Bentley et al., "Accurate Whole Human Genome Sequencing Using Reversible Terminator Chemistry", Nature, vol. 456, No. 7218, Nov. 6, 2008, pp. 53-59.

(Continued)

*Primary Examiner* — Narayan K Bhat
(74) *Attorney, Agent, or Firm* — Kilpatrick Townsend & Stockton LLP

(57) ABSTRACT

Provided herein and methods and apparatuses for sequencing nucleic acids. For example, provided is an analytical detection apparatus, including (a) a stage configured to support a flow cell; (b) a detector configured to observe a detection channel of the flow cell when the flow cell is supported by the stage; (c) a plurality of fluid delivery channels, wherein each of the fluid delivery channels fluidically connects a reservoir to the detection channel of the flow cell; and (d) a first heater configured to heat the plurality of fluid delivery channels.

23 Claims, 18 Drawing Sheets

(56) References Cited

U.S. PATENT DOCUMENTS

| | | |
|---|---|---|
| 2003/0040129 A1* | 2/2003 | Shah .................. B01L 3/5027 506/32 |
| 2008/0108082 A1 | 5/2008 | Rank et al. |
| 2009/0026082 A1 | 1/2009 | Rothberg et al. |
| 2009/0127589 A1 | 5/2009 | Rothberg et al. |
| 2009/0247414 A1 | 10/2009 | Obradovic et al. |
| 2010/0111768 A1 | 5/2010 | Banerjee et al. |
| 2010/0137143 A1 | 6/2010 | Rothberg et al. |
| 2010/0184020 A1* | 7/2010 | Beer ................ B01L 3/502761 435/6.16 |
| 2010/0209925 A1 | 8/2010 | Ishibashi et al. |
| 2010/0282617 A1 | 11/2010 | Rothberg et al. |
| 2012/0270305 A1 | 10/2012 | Reed et al. |
| 2014/0259607 A1 | 9/2014 | Hagerott et al. |
| 2015/0240300 A1* | 8/2015 | Ansari ................ C12Q 1/6869 506/6 |
| 2016/0194697 A1 | 7/2016 | Lee et al. |
| 2016/0199835 A1 | 7/2016 | Tachibana et al. |
| 2017/0022553 A1 | 1/2017 | Vijayan et al. |
| 2017/0191125 A1 | 7/2017 | Vijayan |
| 2017/0314072 A1 | 11/2017 | Vijayan et al. |
| 2018/0044727 A1 | 2/2018 | Vijayan et al. |
| 2018/0155698 A1 | 6/2018 | Iyidogan et al. |
| 2018/0187245 A1 | 7/2018 | Dambacher et al. |
| 2018/0208983 A1 | 7/2018 | Dambacher et al. |
| 2018/0280975 A1 | 10/2018 | Kilcoin et al. |
| 2018/0305749 A1 | 10/2018 | Stromberg et al. |
| 2019/0055596 A1 | 2/2019 | Buermann et al. |
| 2019/0055598 A1 | 2/2019 | Buermann et al. |

FOREIGN PATENT DOCUMENTS

| | | |
|---|---|---|
| WO | 00/63437 | 6/2002 |
| WO | 04/018497 | 3/2004 |
| WO | 05/065814 | 7/2005 |
| WO | 2007/123744 | 11/2007 |

OTHER PUBLICATIONS

PCT/US2019/067647, International Search Report and Written Opinion, dated Aug. 7, 2020, 13 pages.

\* cited by examiner

FIG. 8A

| Speed (uL/s) | Location | Rotary Valve Condition | | Unheated (°C) |
|---|---|---|---|---|
| | | Heated (°C) | Unheated (°C) | |
| 2.5 | T1 | 56.4 | 56.3 | 0.1 |
| 8 | T1 | 54.5 | 53.7 | 0.8 |
| 16 | T1 | 47.5 | 46.3 | 1.2 |
| 64 | T1 | 31.5 | 30.6 | 0.9 |
| 200 | T1 | 24.8 | 24.7 | 0.1 |
| 2.5 | T2 | 51.8 | 49.0 | 2.8 |
| 8 | T2 | 54.5 | 54.5 | 0.0 |
| 16 | T2 | 53.4 | 53.2 | 0.2 |
| 64 | T2 | 40.1 | 39.0 | 1.1 |
| 200 | T2 | 29.7 | 30.1 | -0.4 |
| 2.5 | T3 | 44.1 | 29.5 | 14.6 |
| 8 | T3 | 48.7 | 38.6 | 10.1 |
| 16 | T3 | 50.9 | 43.4 | 7.5 |
| 64 | T3 | 40.3 | 37.2 | 3.1 |
| 200 | T3 | 29.3 | 28.5 | 0.8 |
| 2.5 | T4 | 29.4 | 23.7 | 5.7 |
| 8 | T4 | 36.8 | 30.8 | 6.0 |
| 16 | T4 | 43.8 | 36.7 | 7.1 |
| 64 | T4 | 38.9 | 36.0 | 2.9 |
| 200 | T4 | 28.5 | 26.9 | 1.6 |

FIG. 10A

| Speed (uL/s) | Location | Preheated Condition | | Difference (°C) |
| --- | --- | --- | --- | --- |
| | | 60°C | 70°C | |
| 32 | T1 | 44.5 | 49.77 | 5.27 |
| 64 | T1 | 45.83 | 51.02 | 5.19 |
| 128 | T1 | 46.97 | 52.47 | 5.5 |
| 256 | T1 | 47.81 | 53.68 | 5.87 |
| 384 | T1 | 48.12 | 53.78 | 5.66 |
| 32 | T2 | 40.94 | 45.09 | 4.15 |
| 64 | T2 | 42.38 | 46.42 | 4.04 |
| 128 | T2 | 42.43 | 47.65 | 5.22 |
| 256 | T2 | 44.71 | 48.98 | 4.27 |
| 384 | T2 | 45.14 | 49.47 | 4.33 |
| 32 | T3 | 47.21 | 49.3 | 2.09 |
| 64 | T3 | 48.32 | 50.35 | 2.03 |
| 128 | T3 | 49 | 51.29 | 2.29 |
| 256 | T3 | 49.49 | 51.98 | 2.49 |
| 384 | T3 | 49.51 | 52.25 | 2.74 |
| 32 | T4 | 54.29 | 54.28 | -0.01 |
| 64 | T4 | 54.33 | 54.28 | -0.05 |
| 128 | T4 | 54.44 | 54.54 | 0.1 |
| 256 | T4 | 54.63 | 54.7 | 0.07 |
| 384 | T4 | 54.36 | 54.86 | 0.5 |

TEMPERATURE CONTROL FOR ANALYSIS OF NUCLEIC ACIDS AND OTHER ANALYTES

CROSS-REFERENCE TO RELATED APPLICATION

This application is based on, and claims the benefit of, U.S. Provisional Application No. 62/782,565, filed Dec. 20, 2018, and which is incorporated herein by reference in its entirety.

BACKGROUND

The present disclosure relates generally to detection of chemical and biological analytes and has specific applicability to nucleic acid sequencing.

Accurate sequence determination of a template nucleic acid strand is important for molecular diagnostics. Identification of a single nucleotide base from among alternatives at a known position can serve as the basis for analysis of single nucleotide polymorphisms (i.e., "SNPs"). A SNP can in turn be used to determine a phenotype for the individual such as susceptibility to a disease or propensity for having a desirable trait. Detecting genetic variants in a patient can indicate the efficacy for certain medications to treat the patient or the risk of adverse side effects when treating the patient with certain medications.

Commercially available nucleic acid sequencing platforms have vastly increased our knowledge of the genetic underpinnings of actionable traits. Improvements in sequencing biochemistry and detection hardware continue. However, the cost of currently available sequencing platforms has inhibited uptake of sequencing in the clinic despite broad use in research laboratories. Also, sequencing platforms are relatively slow in terms of providing a diagnostic or prognostic answer on a timeframe that matches expectations of patients and the doctors that treat them.

BRIEF SUMMARY

The present disclosure provides an apparatus for performing an analytical procedure such as determining the sequence of a nucleic acid. The apparatus can include (a) a stage configured to support a flow cell; (b) a detector configured to observe a detection channel of the flow cell when the flow cell is supported by the stage; (c) a plurality of fluid delivery channels, wherein each of the fluid delivery channels fluidically connects a reservoir to the detection channel of the flow cell; and (d) a first heater configured to heat the plurality of fluid delivery channels.

Also provided is an apparatus for sequencing nucleic acids, including (a) a stage in contact with a flow cell, wherein the flow cell comprises at least one detection channel, and wherein the detection channel comprises an array of nucleic acids; (b) a detector configured to observe the array of nucleic acids in the detection channel; (c) a plurality of reservoirs containing reagents for sequencing the array of nucleic acids; (d) a plurality of fluid delivery channels, wherein the fluid delivery channels fluidically connect the plurality of reservoirs to the detection channel of the flow cell; (e) a first heater that transfers heat to the plurality of fluid delivery channels; and (f) a second heater that transfers heat to the detection channel of the flow.

This disclosure further provides a method for performing an analytical procedure such as determining the sequence of a nucleic acid. The method can include steps of (a) providing an analytical apparatus having a flow cell, a fluidic system and a detection system, wherein the flow cell contains an array of analytes, such as nucleic acids, in a detection channel, wherein the fluidic system includes a fluid delivery channel that fluidically connects a reservoir to the detection channel of the flow cell, wherein the detection system observes signals from the array of analytes; (b) transferring a liquid reagent from the reservoir to a heated region of the fluid delivery channel, whereby the liquid reagent is heated; (c) contacting the heated liquid reagent with the array of analytes by transferring the heated liquid reagent to the detection channel; and (d) detecting signals from the array of analytes via the detection system. In nucleic acid sequencing configurations, the liquid reagent is a reagent used for sequencing nucleic acids.

BRIEF DESCRIPTION OF THE DRAWINGS

FIG. 8A shows tabular results obtained from evaluation of thermal properties of fluids prior to entry into a flow cell.

FIG. 10A shows tabular results obtained from evaluation of thermal properties of fluids flowing through a flow cell.

DETAILED DESCRIPTION

Figure 1:
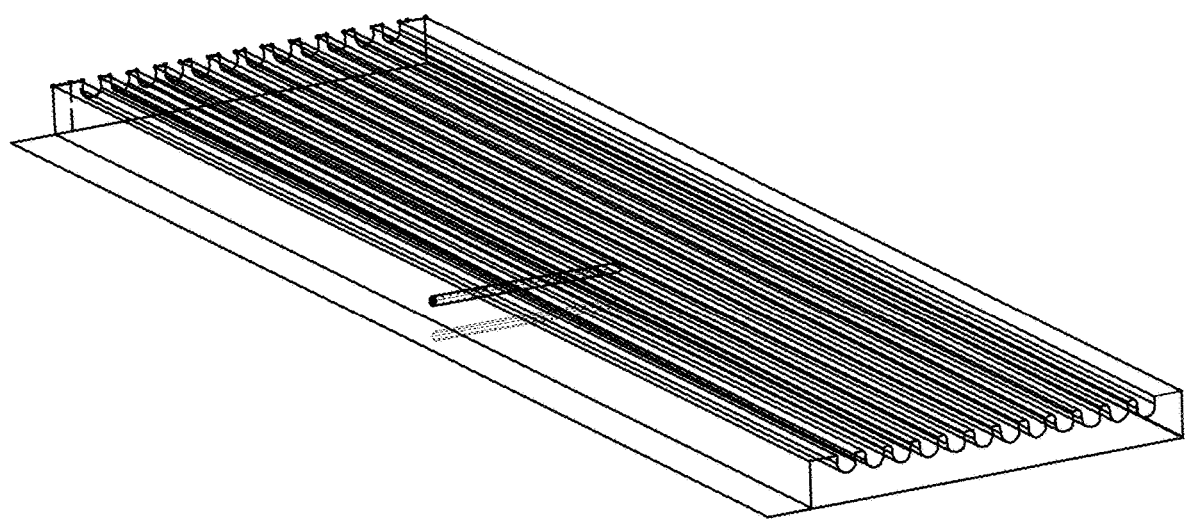
FIG. 1 shows an aluminum heat conductor having a plurality of grooves for heating fluidic tubes.

Many analytical procedures are temperature sensitive. In such cases, temperature fluctuations that are no more extreme than those experienced in the ambient environment of a typical laboratory can adversely impact the results obtained from the analytical procedure. For analyses that use biological components, such as enzymes, the optimal temperature can be elevated compared to the ambient temperature of a typical laboratory. For example, many enzymes that are present in mammals have optimal activity at or near the body temperature of mammals (i.e. about 36° C. to 40° C.). Many useful enzymes, such as polymerases, are derived from thermophiles or are engineered to operate at higher temperatures. Such enzymes can be used in analytical processes that occur at temperatures between 50° C. and 80° C. Changes in temperature from these elevated ranges to the ambient temperature of a typical laboratory can result in significant changes in the activity of reagents used in important analytical processes, such as clinical diagnostic or prognostic tests. As such, it is important to regulate the temperature of analytical processes or apparatuses to obtain high quality results.

A conflicting concern for some analytical apparatuses or processes is instability of reagents at the operating temperature of the apparatus or process. In many cases, it is desired or even necessary to store reagents at reduced temperature prior to use. For example, thermophilic polymerases or other reagents that are used at elevated temperatures of an analytical process, may be stored at room temperature (about 25° C.) or cooler to minimize inactivation prior to use. The reagents can then be heated in a reaction vessel where the analytical process is carried out.

For some analytical processes, reagents that are at a relatively low temperature can be added to a vessel that is at an elevated temperature and the reagents can be allowed to equilibrate until the reagents reach the elevated temperature. Indeed, a wide range of heating apparatus and reaction vessels are available for relatively rapid heating of reaction mixtures, for example, Peltier heaters used in polymerase chain reaction (PCR). However, heating reagents takes time and the impact of increased incubation times on analytical processes can be detrimental.

A unique set of challenges is presented by apparatuses that perform processes that include multiple reagent changes. Nucleic acid sequencing processes provide an example. Many sequencing processes are carried out cyclically such that reagents are delivered and removed from a vessel when detecting each nucleotide in the sequence. Moreover, each cycle typically includes multiple different sub-steps, each sub-step involving delivery of a different reagent to the vessel. Although sequencing reactions often occur at elevated temperatures, many sequencing reagents are not stable at the elevated temperatures and are thus maintained at lower temperature in reservoirs. Commercially available sequencing platforms utilize heated stages to support flow cells or other vessels where sequencing reactions occur and this has been demonstrated to provide satisfactory results.

The present disclosure is based, at least in part, on the observation that nucleic acid sequencing results can be adversely impacted by a temperature difference between the reservoirs where sequencing reagents are stored and a heated flow cell where the sequencing reagents must equilibrate to a different temperature for reaction or detection. The adverse impacts include, for example, base call errors due to side reactions or incomplete sequencing reactions occurring during the time period wherein the reagents are equilibrating to the temperature of the flow cell; inconsistent results observed at different locations of the flow cell due to inconsistent warming of the fluid reagents being flowed (e.g. regions of the flow cell near the fluid ingress have a different temperature from the regions closest to the egress); and aberrant results due to temperature gradients that occur between reagents at the surface of a flow cell that is in contact with a heater and the same type of reagent that is located at the interior volume of the flow cell distal from the heated flow cell surface.

Accordingly, the present disclosure provides fluidics systems, methods and processes that can reduce sequencing time, lower costs of sequencing, reduce reagent volume and provide related advantages as well. For example, an apparatus is provided for performing an analytical procedure such as determining the sequence of a nucleic acid. The apparatus can include (a) a stage configured to support a flow cell; (b) a detector configured to observe a detection channel of the flow cell when the flow cell is supported by the stage; (c) a plurality of fluid delivery channels, wherein each of the fluid delivery channels fluidically connects a reservoir to the detection channel of the flow cell; and (d) a first heater configured to heat the plurality of fluid delivery channels.

An apparatus or method of the present disclosure can utilize a flow cell. As used herein, a "flow cell" is a reaction chamber that includes one or more channels that direct fluid to a detection zone. The detection zone can be functionally coupled to a detector such that a reaction occurring in the channel can be observed. For example, a flow cell can contain primed template nucleic acid molecules tethered to a surface, to which nucleotides and ancillary reagents are iteratively applied and washed away. The flow cell can include a transparent material that permits the sample to be imaged after a desired reaction occurs. For example, a flow cell can include a glass or plastic slide containing detection channels through which polymerases, dNTPs and other fluidic components can be pumped. The glass or plastic inside the channels can be decorated with one or more primed template nucleic acid molecules to be sequenced. An external imaging system can be positioned to detect the molecules at a detection zone in the detection channel or on a surface in the detection channel. Exemplary flow cells, methods for their manufacture and methods for their use are described in U.S. patent application Ser. No. 16/141,896, which was published as US Pat. App. Pub. No. 2019/0055598 A1; US Pat. App. Publ. Nos. 2010/0111768 A1 or 2012/0270305 A1; or WO 05/065814, each of which is incorporated by reference herein.

In a method or apparatus herein, a flow cell can include a solid support to which one or more target analytes or reagents are attached. A particularly useful solid support is one having an array of sites. As used herein, the term "array" refers to a population of molecules that are attached to one or more solid supports such that the molecules at one site can be distinguished from molecules at other sites. An array can include different molecules that are each located at different addressable sites on a solid support. Alternatively, an array can include separate solid supports each functioning as a site that bears a different molecule, wherein the different molecules can be identified according to the locations of the solid supports on a surface to which the solid supports are attached, or according to the locations of the solid supports in a liquid such as a fluid stream. The molecules of the array can be, for example, nucleotides, nucleic acid primers, nucleic acid templates, primed nucleic acid templates or nucleic acid enzymes such as polymerases, ligases, exonucleases or combinations thereof.

As used herein, the term "site," when used in reference to an array, means a location in an array where a particular molecule is present. A site can contain only a single molecule, or it can contain a population of several molecules of the same species (i.e. an ensemble of the molecules). Alternatively, a site can include a population of molecules that are different species (e.g. a population of ternary complexes having different template sequences). Sites of an array are typically discrete. The discrete sites can be contiguous, or they can have interstitial spaces between each other. An array useful herein can have, for example, sites that are separated by less than 100 microns, 50 microns, 10 microns, 5 microns, 1 micron, or 0.5 micron. Alternatively or additionally, an array can have sites that are separated by at least 0.5 micron, 1 micron, 5 microns, 10 microns, 50 microns or 100 microns. The sites can each have an area of less than 1 square millimeter, 500 square microns, 100 square microns, 25 square microns, 1 square micron or less.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, inorganic glasses, optical fiber bundles, and polymers.

Arrays provide the advantage of facilitating multiplex detection. For example, different reagents or analytes (e.g. cells, nucleic acids, proteins, candidate small molecule therapeutics etc.) can be attached to an array via linkage of each different analyte to a particular site of the array. Exemplary array substrates that can be useful include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Further examples of commercially available arrays that can be used include, for example, an Affymetrix GeneChip™ array. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful arrays include those that are used in nucleic acid sequencing applications. For example, arrays that include attached amplicons of genomic fragments (often referred to as clusters), or that are used to create such amplicons, can be particularly useful. Examples of arrays and methods for their manufacture that can be modified for use herein include those described in Bentley et al., Nature 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

An array can have sites that are separated by less than 100 µm, 50 µm, 10 µm, 5 µm, 1 µm, or 0.5 µm. In particular embodiments, sites of an array can each have an area that is larger than about 100 $nm^2$, 250 $nm^2$, 500 $nm^2$, 1 $\mu nm^2$, 2.5 $\mu nm^2$, 5 $\mu nm^2$, 10 $\mu m^2$, 100 $\mu m^2$, or 500 $\mu m^2$. Alternatively or additionally, sites of an array can each have an area that is smaller than about 1 $mm^2$, 500 $\mu m^2$, 100 $\mu m^2$, 25 $\mu m^2$, 10 $\mu m^2$, 5 $\mu m^2$, 1 $\mu m^2$, 500 $nm^2$, or 100 $nm^2$. Indeed, a site can have a size that is in a range between an upper and lower limit selected from those exemplified above. An array can have sites at any of a variety of densities including, for example, at least about 10 sites/$cm^2$, 100 sites/$cm^2$, 500 sites/$cm^2$, 1,000 sites/$cm^2$, 5,000 sites/$cm^2$, 10,000 sites/$cm^2$, 50,000 sites/$cm^2$, 100,000 sites/$cm^2$, 1,000,000 sites/$cm^2$, 5,000,000 sites/$cm^2$, or higher. An apparatus or methods set forth herein can be used to detect an array at a resolution sufficient to distinguish sites at the above densities or site separations.

Although several aspects of apparatus and methods of the present disclosure have been exemplified herein with respect to detecting analytes that are attached to solid supports in a flow cell, it will be understood that analytes need not be attached to a solid support and can instead be detected in a flow cell while in solution phase. Furthermore, flow cells need not be used or even configured for optical detection. Rather, flow cells can be configured for alternative detection modalities using compositions and methods known to those skilled in the art for carrying out those detection modalities.

Several configurations of the instant apparatus and methods utilize optical detection of analytes in a flow cell. Accordingly, a flow cell can include one or more channels each having at least one transparent window, such as an optically transparent window. In particular embodiments, the window can be transparent to radiation in a particular spectral range including, but not limited to one or more of x-ray, ultraviolet (UV), visible (VIS), infrared (IR), microwave and radio wave radiation. In some cases, analytes are attached to an inner surface of the window(s). Alternatively or additionally, one or more windows can provide a view to an internal substrate to which analytes are attached. Exemplary flow cells and physical features of flow cells that can be useful in a method or apparatus set forth herein are described, for example, in US Pat. App. Pub. No. 2010/0111768 A1, WO 05/065814 or US Pat. App. Pub. No. 2012/0270305 A1, each of which is incorporated herein by reference in its entirety.

A flow cell can be made from a material having relatively high thermal conductivity, for example, to allow efficient transfer of heat between the contents of the flow cell and a heater or chiller that is external to the flow cell. Accordingly, the flow cell material can have thermal conductivity that is at least 1 watt per meter-kelvin (W/(m·K), 10 W/(m·K), 100 W/(m·K), 1000 W/(m·K) or higher. Alternatively, the flow cell material can have relatively low thermal conductivity, for example, to help insulate the contents of the flow cell from cooling or heating due to a temperature gradient across the flow cell wall. Accordingly, the flow cell material can have a thermal conductivity that is below 1 W/(m·K). For example, the thermal conductivity can be at most 1 W/(m·K), 0.1 W/(m·K), 0.01 W/(m·K) or lower.

A flow cell can have one or more detection channels. The detection channel(s) can be closed to atmosphere (or other surrounding environment), for example, forming a tube or tunnel inside of the flow cell structure. The detection channel can have any of a variety of cross-sectional shapes including, for example, circular, oval, triangular, square, rectangular, polyhedral or other closed shapes. The cross-sectional area of the detection channel can be uniform over its length. For example, a detection channel having a circular cross-sectional area that is uniform over the length of the channel will have a cylindrical shape, whereas a detection channel having a circular cross-sectional area that is increasing or decreasing over the length of the channel will have a conical or funnel shape. The cross-sectional area of a detection channel can be at least about 1 $\mu m^2$, 10 $\mu m^2$, 100 $\mu m^2$, 1 $mm^2$, 10 $mm^2$, or 100 $mm^2$ or larger. Alternatively or additionally, the cross-sectional area of a detection channel can be at most about 100 $mm^2$, 10 $mm^2$, 1 $mm^2$, 100 $\mu m^2$, 10 $\mu m^2$, 1 $\mu m^2$, or smaller. The volume of a detection channel in a flow cell can be at least about 1 nL, 10 nL, 100 nL, 1 μL, 10 μL, 100 μL, 1 mL, 10 mL or more. Alternatively or additionally, the volume of a detection channel in a flow cell can be at most about 10 mL, 1 mL, 100 μL, 10 μL, 1 μL, 100 nL, 10 nL, 1 nL or less.

In some configurations, a flow cell is a fixed component of a fluidic system, for example, requiring specialized tools and/or specialized training to remove. Alternatively, a flow cell can be a removable component of a fluidic system. For example, an apparatus of the present disclosure can include a stage that is configured for convenient placement and removal of the flow cell. Thus, the flow cell can be a consumable component that is dedicated for use in a first analytical test and then removed to be replaced by a second flow cell used for a second analytical test.

Any of a variety of analytes can be present in a flow cell. Exemplary analytes include, but are not limited to, the analytes set forth herein or in referenced cited herein. Particularly useful analytes participate in nucleic acid sequencing processes. Accordingly, a flow cell can contain one or more nucleic acids (e.g. primers, templates or primed templates), polymerases, polymerase inhibitors, polymerase cofactors, nucleotides, nucleic acid binding proteins, nucleotide deblocking reagents, or the like. In some configurations, a flow cell is provided, the flow cell including a stabilized ternary complex immobilized inside the flow cell, wherein the stabilized ternary complex includes a polymerase, a primed template nucleic acid and a next correct nucleotide for the template.

Fluid reagents can be transferred to a flow cell via a fluidic system that includes at least one fluid delivery channel. In many configurations, several different fluidic reagents are to be delivered to a flow cell. Accordingly, the fluidic system can include a plurality of fluid delivery channels. Individual fluid delivery channels can be dedicated to transferring one type fluid reagent (e.g. from a single reservoir) or alternatively, an individual fluid delivery channel can be configured to transfer more than one different type of fluid reagent (e.g. a single fluidic delivery channel can transfer fluids from two or more different reservoirs).

Fluid delivery channels can be made from any of a variety of materials known in the art of fluidics. Generally, it is preferred to select materials that are inert to the reagents, solvents and other fluidic components that will come into contact with the material when being transferred. For example, the materials can be inert to fluid reagents set forth herein or in references cited herein in the context of nucleic acid sequencing or other analytical processes.

In some configurations the material used for the fluid delivery channel is sufficiently porous to allow transfer of gases through the material (e.g. for degassing purposes) but not so porous as to allow liquids to transfer through the material. Alternatively, a material can be chosen that does not allow passage of gas. The material can be selected for its ability (or inability) to accommodate passage of a particular gas such as one or more of oxygen gas, nitrogen gas, argon gas or atmospheric air.

The apparatus and methods of the present disclosure are particularly useful for low volume fluidic systems such as microfluidic or mesofluidic systems. In microfluidic systems the channels can have inner diameters or widths in the range of about 10 μm to about 1 mm. In mesofluidic systems the channels can have inner diameters or widths in the range of just over 1 mm to about 10 cm. If desired the apparatus or methods of the present disclosure can be applied to higher volume systems such as macrofluidic systems.

In particular configurations, a fluid delivery channel will be heated or chilled. The material for the fluid delivery channel can be selected for favorable properties under the heating or chilling conditions to be used. Exemplary properties of interest include, but are not limited to, chemical stability of the material, structural integrity of the material, flexibility of the material, porosity to degassing, limited expansion, contraction across temperature ranges experienced and the like. The material can be rigid or flexible to suit a particular configuration.

A material for one or more fluid delivery channels can also be selected to have a high thermal activity to allow efficient transfer of heat from a heater to the fluids in the fluid delivery channel. Accordingly, the fluid delivery channel material can have thermal conductivity that is at least 1 watt per meter-kelvin (W/(m·K)), 10 W/(m·K), 100 W/(m·K), 1000 W/(m·K) or higher. Alternatively, the fluid delivery channel material can have relatively low thermal conductivity, for example, to help insulate the contents of the channel from cooling or heating due to a temperature gradient across the channel wall. Accordingly, the fluid delivery channel material can have a thermal conductivity that is below 1 W/(m·K). For example, the thermal conductivity can be at most 1 W/(m·K), 0.1 W/(m·K), 0.01 W/(m·K) or lower.

Exemplary materials that can be used for fluid delivery channels include, but are not limited to, silicone such as Silicon™, Silbrade™ or Tygon™; fluoropolymer such as perfluoroalkoxy (PFA), Teflon™ or polytetrafluoroethylene (PTFE); Polyetheretherketone (PEEK); polyetherimide) (Ultem®); polyethylene; polypropylene; polyurethane; nylon; polyvinylchloride (PVC); metals such as copper or aluminum; carbon fiber or the like.

An apparatus of the present disclosure can further include a heater configured to transfer heat to one or more fluid delivery channels. The heater can be positioned to heat at least a portion of a fluid delivery channel, the portion being upstream of a flow cell. As such, a fluid in the fluid delivery channel will be heated prior to being delivered to the flow cell. Typically, the fluid will have come from a reservoir that was at a lower temperature. For example, the reservoir can maintain the fluid at room temperature (about 25° C.) or at a cooled temperature (less than 25° C., 20° C., 10° C. or 5° C.). The fluid delivery channel can be heated to bring fluids in the channel to a temperature that is higher than the reservoir, for example, the heater for the fluid delivery channel can have a set point that is at least about 30° C., 40° C., 50° C., 60° C., 70° C. or higher than the temperature of the fluid in the reservoir. The heater for the fluid delivery channel can have a set point that is below a particular maximum value such as at most 100° C., 80° C., 70° C., 60° C., 50° C., 40° C., 30° C. or lower. The set point for the fluid delivery channel heater can be a value that is intermediate between the set point for the reservoir and the set point for the flow cell that is connected to the reservoir by the fluid delivery channel. It will be understood that a reservoir can be subject to ambient temperature or the temperature of the reservoir can be controlled by a heater or chiller. The heater or chiller for the reservoir can have a set point that is at a value or in a range of values exemplified herein for a fluid delivery channel heater.

One or more fluid delivery channel(s) can be heated via a heat conductor, whereby heat is transferred via physical contact between a heat source and the channel(s). Alternatively or additionally, a flow cell can be heated via a heat conductor, whereby heat is transferred via physical contact between a heat source and detection channel(s) in the flow cell. The conducting material of the heat source can be a solid, liquid or gel. Exemplary solid materials from which a heat conductor can be made include, but are not limited to, graphene, diamond, aluminum, steel, lead, copper, gold, silver or metal alloys such as aluminum alloys. Exemplary liquid materials from which a heat conductor can be made include, but are not limited to, liquid metals such as mercury; oils; alcohols such as methanol, glycerol, n-propanol or n-butanol; glycols such as ethylene glycol; or water. These liquids can also be circulated past a fluid delivery channel to provide for heating via convection. Exemplary gel materials from which a heat conductor can be made include, but are not limited to, those composed of epoxies, silicones, urethanes, acrylates, aluminum oxide, boron nitride, zinc oxide, or aluminum nitride. Commercially available thermal grease or thermal gel can also be useful.

A fluid delivery channel that is to be heated can pass within the conducting material of a heater, whereby the full exterior perimeter of the portion of the channel that passes through the conducting material is in contact with the material. As such the fluid delivery channel forms a tunnel through the conducting material of the heater. Alternatively, the conducting material can be positioned to contact less than all sides (or less than the full exterior perimeter) of the channel that passes along the conducting material. A solid or gel material that is used to conduct heat to a fluid delivery channel can be shaped for a desired amount of contact with a fluid delivery channel. For example, the solid or gel material can have grooves through which channels pass, ridges between which channels pass, or the like.

FIG. 1 shows an aluminum heat conductor having twelve grooves. The groove plate is configured to heat 12 inch long portions of silicone tubes having 1/32 inch inner diameter and 5/32 inch outer diameter. Grooves can be modified in shape or dimensions to accommodate channels of different size or shape including, but not limited to the shapes or dimensions set forth herein. An individual tube can pass through each groove such that about 180 degrees of the external diameter of the tube is in direct contact with the aluminum. The other 180 degrees of the tube external diameter that is not in contact with the metal can be in contact with surrounding atmosphere. In similar configurations, the grooves and tubes can be fitted to contact or conductively heat at least 10%, 25%, 50%, 75%, 90%, 99% or more of the outer diameter (or localized perimeter of non-cylindrical channels) of the channel. Alternatively or additionally, the grooves and tubes can be fitted to contact or conductively heat at most 99%, 90%, 75%, 50%, 25%, 10% or less of the outer diameter (or localized perimeter of non-cylindrical channels) of the channel. In some configurations the full exterior surface of the channel is in contact with the heater.

A groove plate can be heated via contact with a heater element. For example, the groove plate of FIG. 1 can be heated via four 3 inch by 3 inch, 24 VDC heat pads. The groove plate configuration allows for a relatively large contact area for heat conduction, while allowing for transfer of gas through the rest of the external surface of the tube. As such the fluid in the tube can be degassed while being heated. Degassing can be facilitated by placing at least a portion of the fluid delivery channel, for example, a portion that is heated or a portion that is downstream from a heat source, in a vacuum jacket or gas flow jacket. The vacuum or flow of gas can function to dissipate the gases that exit through the porous wall of the channel, thus pulling gas through the porous material from the inside of the fluid delivery channel. Removal of gases from the environment outside of the channel can pull gases through the channel wall in accordance with the law of mass action.

One or more fluid delivery channel(s) can be heated via a heat radiator or convection heater, whereby heat is transferred absent direct contact between a heat source and the channel(s). Alternatively or additionally, a flow cell can be heated via a heat radiator or convection heater, whereby heat is transferred absent physical contact between a heat source and detection channel(s) in the flow cell.

Another option for heating fluid delivery channels is to use a Joule heater instead of a heat pad. The Joule heater can have one or more heating elements that contact a fluid delivery channel, for example, the element can run parallel to the fluid delivery channel. The heating element of the Joule heater can be present in a groove plate, for example, forming part of the base of the plate or part of a ridge that defines a groove, or the element can be used instead of a groove.

A fluid delivery channel and its heater can be insulated to minimize heat loss. For example, a heated block, heating element and fluid delivery channel can be surrounded by insulating material to prevent excess heat from radiating away from the preheater. This can provide a benefit of reducing power consumption and thermally isolating the preheater from surrounding components.

One or more fluid delivery channel(s) can be heated via a convection heater, whereby heat is transferred from a heated fluid (i.e. liquid or gas) that moves past the external wall of the fluid delivery channel(s). The convection heater can transfer heat from a circulating fluid to the external wall of the fluid delivery channel that contacts the fluid. Similarly, one or more detection channels in a flow cell can be heated via a convection heater, whereby heat is transferred from a heated fluid (i.e. liquid or gas) that moves past the external wall of the detection channel(s). The convection heater can transfer heat from a circulating fluid to the external wall of the detection channel that contacts the fluid. The fluids used for convection heating can be selected from the liquids exemplified above for conduction heating. Any of a variety of gases can be used for convection heating including, for example, inert gases such as argon, nitrogen, helium or neon, mixed gases such as atmospheric air, and other gases.

One or more fluid delivery channel(s) can be heated via a heat radiator, whereby heat is transferred from a heat source that is proximal to the channel(s). Heat radiation can be particularly useful when heating a fluid delivery channel through a vacuum (e.g. through a vacuum jacket) or through a gas (e.g. through a gas flow jacket)

A heater for a fluid delivery channel can be thermally isolated from one or more other component of an apparatus set forth herein. For example, a flow cell can be insulated such that the external surface of the flow cell does not receive heat directly from the heater that is used to heat a fluid delivery channel. In this configuration, the flow cell may be heated due to ingress of fluid that is heated by the fluid delivery channel heater, but heat transfer to the exterior of the flow cell would not be substantial except via indirect means such as via the fluid inside the flow cell. The heater for the fluidic delivery channel can be thermally isolated from other components of an analytical apparatus such as computer processors, reagent reservoirs, detectors, electronics and the like. Accordingly, a heater and a fluidic delivery channel that it will heat can be present in a chamber that is isolated from one or more chambers where other components reside. Similarly, a heater for a flow cell can be thermally isolated from one or more other components of an apparatus set forth herein. For example, one or more fluid delivery channels can be insulated from receiving heat directly from a heater that is used to heat a flow cell.

Optionally, a heater that directly heats a fluid delivery channel can be configured to also directly heat another component of an apparatus set forth herein. For example, a heater can be configured to directly heat a fluid delivery channel and a flow cell. The heater can heat multiple system components by the same mechanism (e.g. conduction, convection or radiation). Continuing with the previous example, the heater can physically contact both the fluid delivery channel and the flow cell to transfer heat to both via conduction. For example, a fluid delivery channel can pass along a first side of a heated block and a flow cell can be placed on a second side of the block or the flow cell can be placed at another location on the same side of the block as the fluid delivery channel. Alternatively, two different components can receive heat from the same heater, albeit via different mechanisms. For example, the heater can be in direct contact with the fluid delivery channel to transfer heat via conduction and the heater can be proximal to the flow cell to deliver heat via radiation or convection. Accordingly, the external surface of a fluid delivery channel (or a portion thereof) and the external surface of a flow cell (or a portion thereof) can be present in the same chamber when heated. Conversely, a heater can be in direct contact with a flow cell to transfer heat via conduction and the heater can be proximal to one or more fluid delivery channels to deliver heat via radiation or convection. In some configurations the radiative or conductive heat can be transferred to a valve such as a rotary valve.

A heater can be configured to heat a defined internal volume of a fluid delivery channel. In cases where fluid comes to rest in the delivery channel, the volume of fluid heated can be roughly equivalent to the volume of the channel interior that is heated. The internal volume of the fluid delivery channel that is heated can be less than, equivalent to, or greater than the internal volume of a detection channel in a flow cell to which the heated fluid will be transferred. For example, the internal volume of a fluid channel can be at least 10%, 50%, 90%, 100%, of the volume of the detection channel or at least 2×, 3×, 5×, 10× or more than the volume of the detection channel. Alternatively or additionally, the internal volume of a fluid channel can be at most 10×, 5×, 3×, or 2× larger than the volume of the detection channel or at most 100%, 90%, 50%, 10% or smaller than the volume of the detection channel. A heater can be configured to heat an equivalent internal volume for one or more fluid delivery channels. Alternatively, fluid reagents used in a method or apparatus set forth herein can differ with respect to the volume of the fluid that is to be heated. Accordingly, the fluid delivery channels can differ with regard to the internal volume that will be heated. Optionally, a first subset of fluid delivery channels can be heated and a second subset of fluid delivery channels can be substantially isolated or insulated from any or all dedicated heat sources.

A fluid need not come to rest in a fluid delivery channel when being heated. Rather, the fluid flow rate can be tailored in view of the set point temperature of the heater and other characteristics of the heater and fluidic system to achieve a desired temperature for fluids when entering the detection channel of a flow cell. Whether the fluid is at rest or flowing when heated, the apparatus can be configured to heat a volume of fluid that is equivalent to at least 10%, 50%, 90%, 100%, 2×, 3×, 5×, 10× or more than the volume of the detection channel. Alternatively or additionally, the apparatus can be configured to heat a volume of fluid that is equivalent to at most 10×, 5×, 3×, 2×, 100%, 90%, 50%, 10% or less than the volume of the detection channel. A heater can be configured to heat an equivalent volume for one or more fluid delivery channels. Alternatively, fluid reagents used in a method or apparatus set forth herein can differ with respect to the volume of the fluid that is to be heated. Either result can be achieved by adjusting one or more of the internal volume of the channels that is heated, the temperature of the heater, the thermal conductivity of the fluid delivery channel, and the flow rates for the fluids passing through the heated portions of the channels.

The temperature of the fluid delivery channels can be regulated, for example, via a thermostat. The thermostat can be configured to measure the temperature of the heated component of the heater (e.g. groove plate, solid phase block, or liquid bath), the surface of one or more fluid delivery channel, or the fluid that passes through the heated portion of a fluid delivery channel. The temperature of the fluid can be detected in the portion of the fluid delivery channel that is heated or at a point downstream of the heated portion. In some configurations multiple temperature detectors can be used, for example, being positioned in the heated portion of the channel, at the exit of the heated portion and at one or more locations downstream of the heated portion. One or more temperature detectors can be upstream of the heated portion. A particularly useful thermostat uses a thermocouple, such as a Type K thermocouple or Type J thermocouple. Exemplary temperature sensors and exemplary placements in a fluidic system are set forth in Example II below. Such sensors can be used in a thermostat for regulating temperature of a fluid delivery channel heater.

Fluid pressure can be regulated in an apparatus or method of the present disclosure. Pressure sensors can be configured to detect pressure and provide a feedback loop to adjust pressure to a desired level. Pressure sensors can be placed at similar locations to those set forth herein with regard to temperature sensors. For example, a pressure sensor can be placed downstream or upstream of a fluid delivery channel, downstream or upstream of a fluid delivery channel heater, downstream or upstream of a flow cell, downstream from a reagent reservoir or upstream of a waste reservoir.

An apparatus of the present disclosure can include one or more reservoirs. The reservoirs can be open to atmosphere and accessed by lowering an array of sippers into the reservoirs. The reservoirs can be made from any of a variety of materials including, but not limited to, those set forth herein in regard to fluid delivery channels, flow cells or arrays. The reservoirs are generally fully enclosed. This can provide the advantages of avoiding contamination. If desired the reservoirs can be pressurized, for example, to suppress degassing of the reagents that would otherwise cause unwanted bubble formation in downstream fluidic components. Pressurizing can also provide the advantage of driving fluids from the reservoirs to the flow cell. Screw top bottles are particularly useful but other chambers can be used as well. The reservoirs can be permanently fixed to the apparatus, individually accessible for placement or removal from a larger apparatus or combined into a fluidic cartridge or caddy that allows convenient bulk placement or removal of several reservoirs at once. The reservoirs can contain reagents set forth herein or in references cited herein for use in a sequencing process or other analytical process.

Each reservoir may have a dedicated fluid delivery channel. One or more of the fluid delivery channels can be heated as set forth herein prior to the fluid being transferred to a flow cell. The use of fluid delivery channels that are dedicated to a particular fluid reagent, for example, by being dedicated to a single reservoir can provide the benefit of minimizing unwanted cross reactions upstream of the flow cell and allowing individualized control of flow characteristics (e.g. flow rates, total volumes heated or total volumes delivered to the flow cell) or heating characteristics (e.g. heating rates, or final temperatures). One or more reservoirs can share a fluid delivery channel that is to be heated prior to the fluid being transferred to a flow cell. This configuration can provide efficient fluid processing, for example, when uniform flow characteristics or heating characteristics are used across several fluid reagents.

Preheating of reagents can occur in a common fluidic delivery channel. The common fluidic delivery channel can connect a plurality of reservoirs, for example, via a manifold. As such, heating of a fluid delivery channel can occur downstream from a manifold. This configuration can be useful when heating can be achieved quickly, in which case the heated portion of the common fluidic delivery channel can optionally be immediately upstream of the flow cell. In alternative configurations, heating does not occur at a common fluidic delivery channel and is instead localized to portions of the fluidic system that are upstream of a common fluidic delivery channel, manifold or rotary valve.

Multiple different fluid delivery channels can be merged for entry into the detection channel of a flow cell using a manifold. The manifold can be placed downstream of a fluid delivery channel heater and upstream of the ingress for the detection channel. The flow of fluid from one or more of the fluid delivery lines to the detection channel can be controlled by a valve. In particular configurations, a rotary valve can function to select one of a plurality of fluid delivery channels for fluid flow to the detection channel. Other valves that can be used include, for example, a ball valve, diaphragm valve, choke valve, butterfly valve, pinch valve, solenoid valve or the like.

A valve or manifold can optionally be heated. The heater can be of a type set forth herein in relation to heating a fluid delivery channel or flow cell. The set point for a valve or manifold heater can be the same as, higher than or lower than the set point for an upstream fluidic delivery channel heater. The set point for a valve or manifold heater can be the same as, higher than or lower than the set point for a downstream flow cell heater. The set point for the valve or manifold heater can be intermediate to the set point for the upstream fluid delivery channel heater and the set point for the downstream flow cell heater. As such, the three heaters can establish a temperature gradient that increases with the direction of flow or that decreases with the direction of flow. The configuration can be selected to achieve a desired final temperature in the flow cell for a particular reaction or for one or more steps of an analytical process.

An apparatus of the present disclosure can include a pump configured to drive fluids through fluid delivery channels, flow cells or other components. Syringe pumps can be particularly useful. Other types of devices besides syringe pumps can be used to drive fluids including, for example, positive or negative pressure, peristaltic pump, diaphragm pump, piston pump, gear pump or Archimedes screw. A pump can be configured to apply positive fluid displacement (e.g. via positive pressure) to push fluids from a reservoir, fluid delivery channel or other fluidic component and into the flow cell. Alternatively, a pump can be configured to apply negative fluid displacement (e.g. via negative pressure) to pull fluids from a flow cell into other fluidic components such as a waste container or cache for recycling reagents. Particularly useful pumps include, for example, those used in sequencing platforms set forth herein or in references cited herein.

A pump can be positioned upstream of a reservoir and flow cell between a reservoir and flow cell or downstream of a reservoir and flow cell. When the pump is upstream of the reservoir and flow cell, the pump will push fluid from the reservoir to the flow cell. If the pump is positioned between a reservoir and flow cell, the pump will pull fluid from the reservoir and push the fluid to the flow cell. If the pump is placed downstream of a reservoir and flow cell, the pump will pull fluid from the reservoir and to the flow cell.

An apparatus of the present disclosure can include a stage configured to support a flow cell. The stage can be configured to position the flow cell with respect to fluidic components of the apparatus and/or detector components of the apparatus. Optionally, the stage can be configured to move the flow cell, for example, to allow the contents of the flow cell to be observed by scanning. The stage can be capable of movement in one or more of the x, y and z directions in a Cartesian coordinate system. For purposes of this disclosure, the z axis will be the axis along which changes in focus are achieved (i.e. the axis that runs along the distance between the detector and flow cell surface), the x axis will be the direction along which the flow cell is scanned and the y axis will be orthogonal to the z and x axes. In addition to linear motions along x, y and z axes, a stage can be capable of rotating a flow cell. Rotation around the z axis will be referred to as yaw, rotation around the x axis will be referred to as roll and rotation around the y axis will be referred to as pitch. These dimensions and movements are illustrated in FIG. 1 of U.S. patent application Ser. No. 16/141,896, which is published as US Pat. App. Pub. No. US 2019/0055598 A1 and which is incorporated herein by reference. Any of a variety of stages can be used such as those common to laboratory microscopes or nucleic acid sequencing platforms. Examples of useful stages include those disclosed in references incorporated below in the context of detection apparatus of nucleic acid sequencers.

A particularly useful stage is configured to slide a flow cell along a reference surface, for example, using apparatus and methods set forth in U.S. patent application Ser. No. 16/141,896, which is published as US Pat. App. Pub. No. US 2019/0055598 A1 and which is incorporated herein by reference. Such apparatus and methods can provide a benefit of avoiding the use of high precision actuators that are adjustable in a variety of translational and rotational directions. High precision actuators add cost and complexity to a scanner, and such rigs typically require highly trained technicians for routine maintenance. The flow cell stages set forth in U.S. patent application Ser. No. 16/141,896 (US Pat. App. Pub. No. US 2019/0055598 A1) avoid such issues by decoupling the mechanism that is used to translate a flow cell with respect to a detector from the mechanism that is used to rotationally register the flow cell with respect to the detector. Decoupling translation from rotational registration reduces the tolerance stack for the translation mechanism in detection apparatus and other apparatus of the present disclosure.

A further advantage of using a flow cell stage of U.S. patent application Ser. No. 16/141,896 (US Pat. App. Pub. No. US 2019/0055598 A1) is that the flow cell can be scanned more quickly. The increase in scanning speed is, in large part, a function of the flow cell translation apparatus being configured to move a mass that is smaller than a typical stage. A small mass takes less time to settle compared to a larger mass that is moved the same distance. For example, the time spent waiting for a flow cell to settle prior to acquiring an image becomes increasingly significant as the desired resolution for detection increases because the motion of the flow cell must dampen to a point that the average displacement experienced by features of the object under observation is small enough to preclude substantial distortions in the image.

A flow cell stage can include a reference surface, a preload and a scan actuator, wherein the preload is configured to urge the flow cell to contact the reference surface during a detection event, wherein the reference surface forms a fixed structural loop with the detector, and wherein the scan actuator is configured to slide the flow cell along the reference surface in a scan dimension. Accordingly, the detection apparatus used in an apparatus of the present disclosure can include (a) a flow cell having a lumen and a wall, wherein the wall has an internal surface and an external surface, wherein the internal surface contacts the lumen; (b) a reference surface that forms a fixed structural loop with a detector; (c) a preload configured to urge the external surface of the flow cell to contact an area on the reference surface; (d) a scan actuator configured to slide the flow cell along the reference surface in a scan dimension; and (e) a transmitter configured to direct, to the detector, a signal from the internal surface or the lumen, when the external surface of the flow cell is urged by the preload to contact the reference surface.

As provided herein, a detection apparatus can include (a) a flow cell having a lumen and a wall, wherein the wall has an internal surface and an external surface, wherein the internal surface contacts the lumen, and wherein the external surface has length l in a scan dimension x; (b) a reference surface; (c) a preload configured to urge the external surface of the flow cell to contact an area on the reference surface, optionally the area of contact can have a maximum length in the scan dimension x that is shorter than length l; (d) a scan actuator configured to slide the flow cell along the reference surface in the scan dimension x; (e) a detector; and (f) an objective configured to direct radiation from the flow cell to the detector when the external surface of the flow cell is urged by the preload to contact the reference surface.

A flow cell can be scanned using steps of (a) translating the flow cell along a reference surface of a detection apparatus, wherein the flow cell has a lumen and a wall, wherein the lumen comprises analytes, wherein the reference surface contacts at least a portion of the flow cell during the translating, and wherein the reference surface forms a fixed structural loop with a detector; and (b) detecting the analytes at different locations along the flow cell using the detector, wherein the flow cell is urged to the reference surface by a preload during the detecting, thereby scanning the flow cell.

An apparatus of the present disclosure can include a heater that is configured to heat a flow cell that is supported by the stage. The heater can be separate and independent from a heater that is used to heat a fluid delivery channel. Alternatively, and as set forth above, the same heater can be used to heat a flow cell and to heat a fluid delivery channel. A flow cell heater can be selected from among the same types that are exemplified herein for use to heat a fluidic delivery channel, valve or manifold. The flow cell heater can be an integral component of a flow cell stage or it can be a separate device that is positioned to deliver heat to the flow cell when it is present on the stage.

Optionally, a heating element can be integrated into a flow cell. For example, a flow cell can contain one or more thermal channels through which a heated fluid phase flows. Alternatively or additionally, a flow cell can contain a solid-phase heating element such as a wire, coil or filament. Optionally a heating element can be positioned at the upstream region of the flow cell, for example, adjacent to the ingress of a detection channel. In another option a heating element can be positioned along the length of one or more detection channel.

A flow cell heater can have a set point that is lower than, equivalent to, or higher than the set point of the heater for one or more fluidic delivery channels. For example, the set point for a flow cell heater can have a set point that is at least about 30° C., 40° C., 50° C., 60° C., 70° C. or higher. The flow cell heater can have a set point that is below a particular maximum value such as at most 100° C., 80° C., 70° C., 60° C., 50° C., 40° C., 30° C. or lower.

In relative terms the set point for a fluidic delivery channel heater can be higher than the set point for a flow cell heater, for example, by at least about 5° C., 10° C., 20° C., 30° C., or 50° C. or higher. Alternatively or additionally, the set point for a fluidic delivery channel heater can be at most about 50° C., 30° C., 20° C., 10° C., or 5° C. higher than the set point for a flow cell heater.

Conversely, the set point for a flow cell heater can be higher than the set point for a fluidic delivery channel heater, for example, by at least about 5° C., 10° C., 20° C., 30° C., or 50° C. or higher. Alternatively or additionally, the set point for a flow cell heater can be at most about 50° C., 30° C., 20° C., 10° C., or 5° C. higher than the set point for a fluidic delivery channel heater.

Thus, the temperature of a fluid delivery channel can be the same as or different from the temperature of a flow cell. Optionally, the temperature of a fluid delivery channel is the same as the temperature of a flow cell. The temperature of a fluid delivery channel can be higher or lower than the temperature of the flow cell. Further, the temperature of a fluid delivery channel and/or a flow cell can be higher than the temperature of a reservoir.

The temperature of the flow cell can be regulated, for example, via a thermostat. The thermostat can be configured to measure the temperature of the heated component of the heater (e.g. heated stage), the surface of one or more region of the flow cell (e.g. a region through which or past which one or more detection channels passes), or the fluid that passes through the heated portion of the flow cell. The temperature of the fluid can be detected in the portion of the detection channel that is heated or at a point downstream of the heated portion. In some configurations multiple temperature detectors can be used, for example, being positioned in the heated portion of the flow cell, at the exit of the heated portion and at one or more locations downstream of the heated portion. A particularly useful thermostat uses a thermocouple, such as a Type K thermocouple or Type J thermocouple. Exemplary temperature sensors and exemplary placements in a fluidic system are set forth in Example II below. Such sensors can be used in a thermostat for regulating temperature of a flow cell heater.

An apparatus set forth herein can employ optical subsystems or components used in nucleic acid sequencing systems to detect analytes in a flow cell. Several such detection apparatus are configured for optical detection, for example, detection of fluorescent signals. Examples of detection apparatus and components thereof that can be used to detect a flow cell herein are described, for example, in U.S. patent application Ser. No. 16/141,896; US Pat. App.

Pub. No. 2010/0111768 A1 or U.S. Pat. Nos. 7,329,860, 8,951,781 or 9,193,996, each of which is incorporated herein by reference. Other detection apparatus include those commercialized for nucleic acid sequencing such as those provided by Illumina™, Inc. (e.g. HiSeg™, MiSeg™, NextSeg™, or NovaSeg™ systems), Life Technologies™ (e.g. ABI PRISM™, or SOLiD™ systems), Pacific Biosciences (e.g. systems using SMRT™ Technology such as the Sequel™ or RS II™ systems), or Qiagen (e.g. Genereader™ system). Other useful detectors are described in U.S. Pat. Nos. 5,888,737; 6,175,002; 5,695,934; 6,140,489; or 5,863,722; or US Pat. Pub. Nos. 2009/0247414 A1, or 2010/0111768; or WO2007/123744, each of which is incorporated herein by reference in its entirety.

Particularly useful optical detection systems will employ an objective having a numerical aperture that is at least 0.1 and at most 0.9. Numerical apertures above 0.95 can be achieved using an immersion objective as set forth in further detail below. An objective can be configured to operate with a detection system that resolves features (e.g. nucleic acid sites) on a surface that are separated by less than 100 µm, 50 µm, 10 µm, 5 µm, 1 µm, or 0.5 µm. The detection system, including objective, can be configured to resolve features having an area on a surface that is smaller than about 1 mm$^2$, 500 µm$^2$, 100 µm$^2$, 25 µm$^2$, 10 µm$^2$, 5 µm$^2$, 1 µm$^2$, 500 µm$^2$, or 100 nm$^2$.

An optical system used in an apparatus or method set forth herein can have a field of view that is at least 0.1 mm$^2$, 0.5 mm$^2$, 1 mm$^2$, 2 mm$^2$, 3 mm$^2$, 4 mm$^2$ or higher. Alternatively and/or additionally, the field of view can be configured to be at most 4 mm$^2$, 3 mm$^2$, 2 mm$^2$, 1 mm$^2$, 0.5 mm$^2$, 0.1 mm$^2$, or less.

A detector that is used to observe a flow cell in a method or apparatus set forth herein need not be capable of optical detection. For example, the detector can be an electronic detector used for detection of protons or pyrophosphate (see, for example, US Pat. App. Pub. Nos. 2009/0026082 A1; 2009/0127589 A1; 2010/0137143 A1; or 2010/0282617 A1, each of which is incorporated herein by reference in its entirety, or the Ion Torrent™ systems commercially available from ThermoFisher, Waltham, Mass.) or as used in detection of nanopores such as those commercialized by Oxford Nanopore™, Oxford UK (e.g. MinION™ or PromethION™ systems) or set forth in U.S. Pat. No. 7,001,792; Soni & Meller, *Clin. Chem.* 53, 1996-2001 (2007); Healy, *Nanomed.* 2, 459-481 (2007); or Cockroft, et al. *J. Am. Chem. Soc.* 130, 818-820 (2008), each of which is incorporated herein by reference.

Control of system components such as heaters, thermostats, pumps or detectors, can utilize a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Optionally, an apparatus of the present disclosure can include a computer processing unit (CPU) that is configured to operate one or more of the system components set forth herein. The same or different CPU can interact with the system to acquire, store and process signals (e.g. signals detected in a method set forth herein). In particular embodiments, a CPU can be used to determine, from the signals, the identity of the nucleotide that is present at a particular location in a template nucleic acid. In some cases, the CPU will identify a sequence of nucleotides for the template from the signals that are detected.

A useful CPU can include, for example, one or more of a personal computer system, server computer system, thin client, thick client, hand-held or laptop device, multiprocessor system, microprocessor-based system, set top box, programmable consumer electronic, network PC, minicomputer system, mainframe computer system, smart phone, or distributed cloud computing environment that includes any of the above systems or devices. The CPU can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The CPU may also include a variety of computer system readable media. Such media may be any available media that is accessible by a cloud computing environment, such as volatile and non-volatile media, and removable and non-removable media.

The memory architecture of a processor used herein may include at least one program product having at least one program module implemented as executable instructions that are configured to control one or more component of an apparatus set forth herein or to carry out one or more portions of a method set forth herein. For example, executable instructions may include an operating system, one or more application programs, other program modules, and program data. Generally, program modules may include routines, programs, objects, components, logic, data structures, and so on, that perform particular tasks such as controlling hardware carrying out a step set forth herein or processing of signals detected by an apparatus or method set forth herein.

The components of a computer processor may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A CPU can optionally communicate with one or more external devices such as a keyboard, a pointing device (e.g. a mouse), a display, such as a graphical user interface (GUI), or other device that facilitates interaction of a user with an apparatus set forth herein. Similarly, the CPU can communicate with other devices (e.g., via network card, modem, etc.). Such communication can occur via I/O interfaces. Furthermore, a CPU of a system herein may communicate with one or more networks such as a local area network (LAN), a general wide area network (WAN), and/or a public network (e.g., the Internet) via a suitable network adapter.

Optionally, a proportional integral derivative (PID) controller can be used to regulate temperature, fluid flow, pressure, speed and other process variables. A PID controller can be configured to use a control loop feedback mechanism to control the process variables. By way of more specific example, a PID controller can be used to control a feedback loop that includes a temperature sensor or pressure sensor that is used in an apparatus or method herein.

A bubble sensor can also be used, for example, to mitigate unwanted bubbles. An example of a bubble sensor configuration is to place a bubble sensor upstream of a rotary valve and upon detection of a bubble or upon reaching a threshold level of bubbles, the valve can be activated to divert the bubble(s) away from a flow cell or other vessel where bubbles would have an adverse consequence. In response to detection of bubble(s), the fluidic system can also respond by increasing pressure on the fluids, decreasing flow rate of the fluid, decreasing temperature of the fluid or taking other mitigating steps to remove or avoid the bubble(s).

Figure 14A:
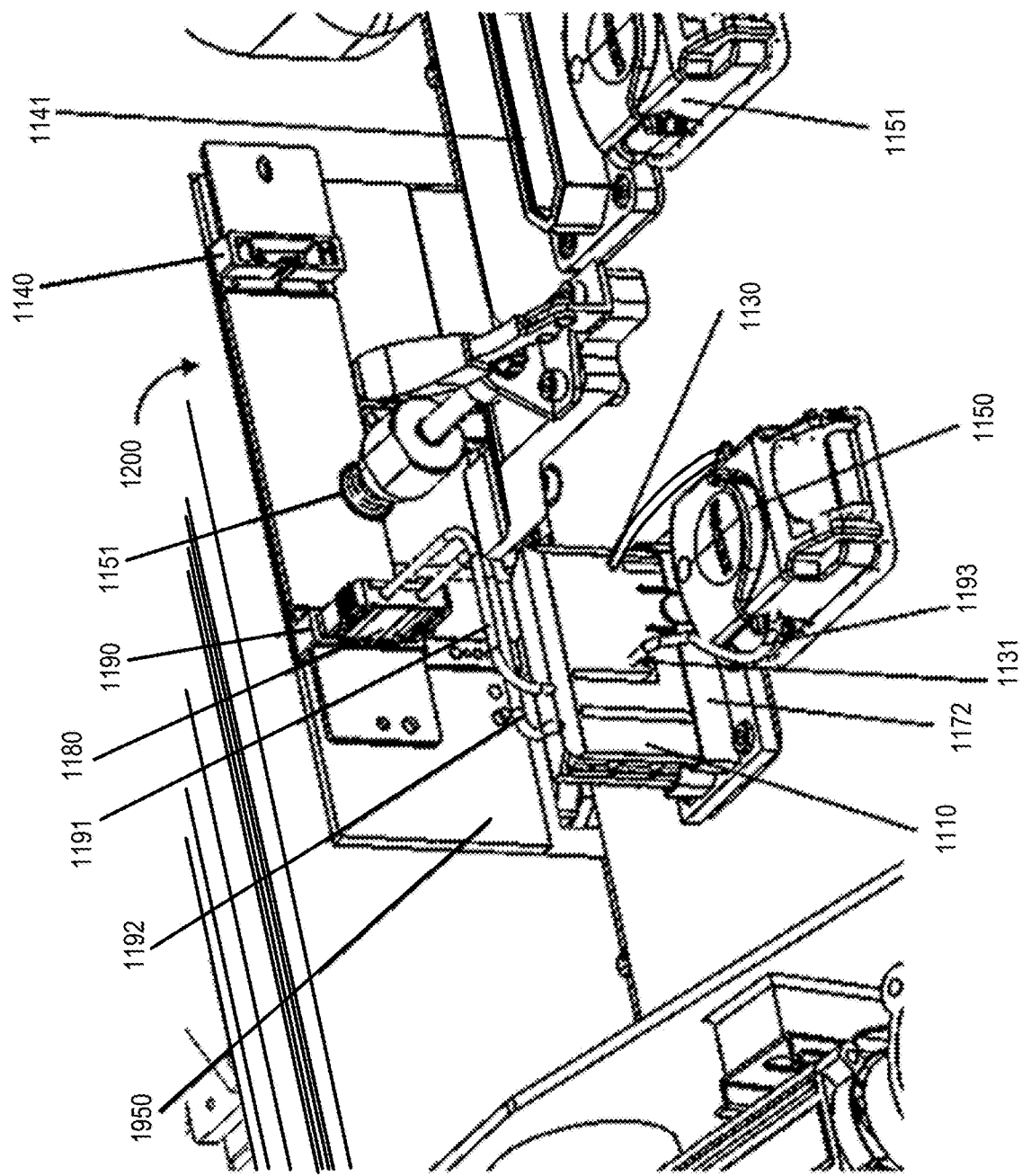
FIG. 14A shows a perspective view of the fluidic connection between a nucleic acid sequencing system and a flow cell.
Figure 14B:
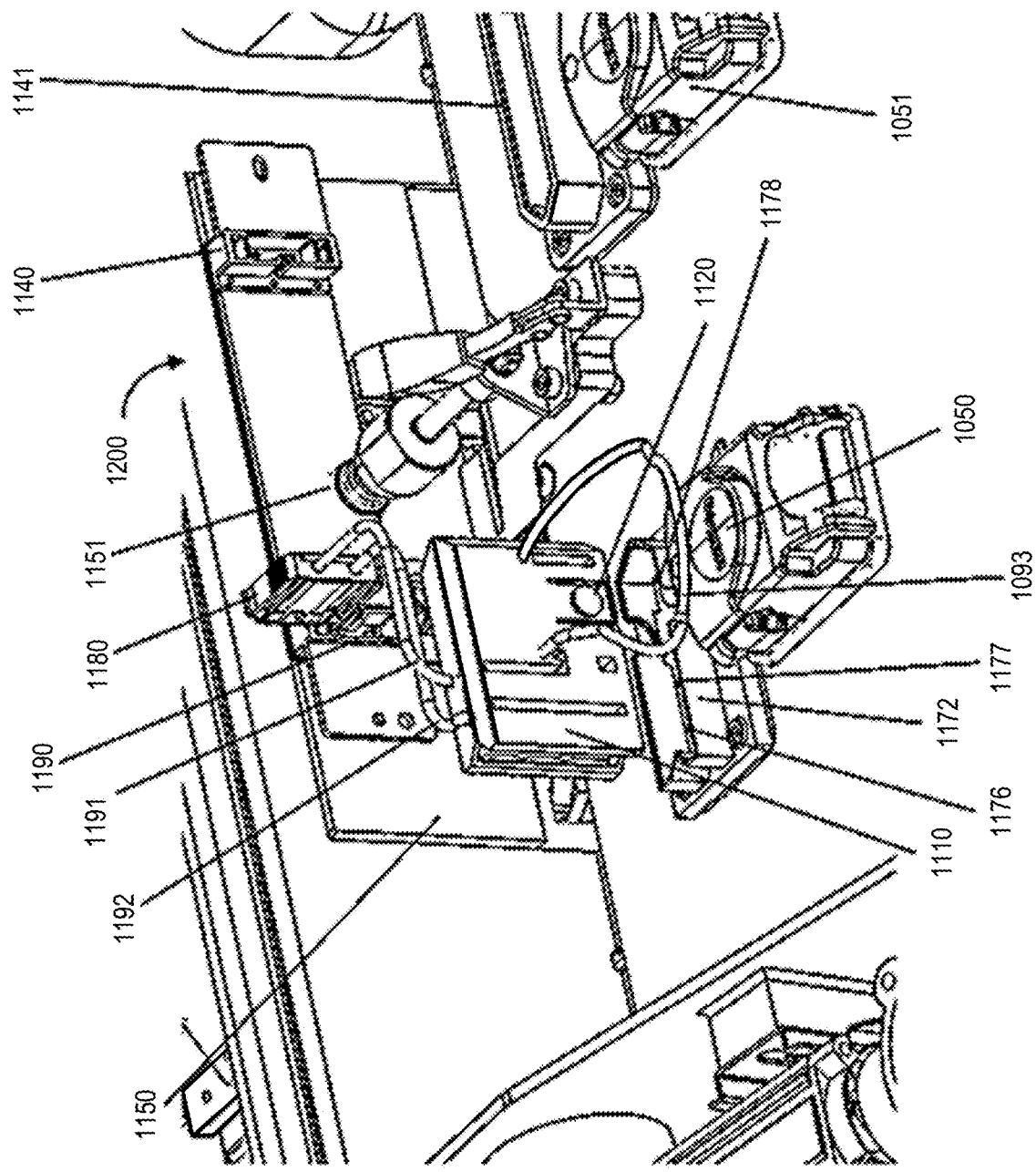
FIG. 14B shows the same perspective, but with the connectors disconnected.

However, not all bubbles are unwanted. In fact, apparatuses provided herein can include a bubble sensor and a bubble generator when bubbles are desired. The bubble sensor can be used to detect and remove bubbles outside of desired bubble characteristics. Suitable bubbles for use in the provided apparatuses, exemplary bubble generators, other hardware and methods for using foam to sequence nucleic acids and to perform other analytical procedures are set forth in U.S. patent application Ser. No. 16/700,422, which is incorporated herein by reference. For example, in particular configurations a bubble generator can be housed within instrument connector 1110 (FIGS. 14A and 14B).

This disclosure provides a method for sequencing nucleic acids. The method can include steps of (a) providing a sequencing apparatus having a flow cell, a fluidic system and a detection system, wherein the flow cell contains an array of nucleic acids in a detection channel, wherein the fluidic system includes a fluid delivery channel that fluidically connects a reservoir to the detection channel in the flow cell, wherein the detection system observes signals from the array of nucleic acids; (b) transferring a sequencing reagent from the reservoir to a heated region of the fluid delivery channel, whereby the sequencing reagent is heated; (c) contacting the heated sequencing reagent with the array of nucleic acids by transferring the heated sequencing reagent to the detection channel; and (d) detecting signals from the array of nucleic acids via the detection system. The sequencing reagent can be a fluidic sequencing reagent, e.g., a liquid sequencing reagent.

The present disclosure provides methods and apparatus that are particularly useful for performing cyclical reactions. Each cycle can include delivering reagents for the reaction to a flow cell where, optionally, the reaction, or products of the reaction, will be observed. Each cycle can further include heating or chilling fluid reagents or components of the fluidic system using apparatus or methods set forth herein. The methods and apparatus of the present disclosure are exemplified herein in the context of performing nucleic acid sequencing reactions. However, those skilled in the art will understand from the teaching herein how to modify the methods, and the apparatus, for other cyclical reactions such as nucleic acid synthesis reactions, peptide sequencing reactions, peptide synthesis reactions, combinatorial small molecule synthesis reactions or the like. However, the method need not be cyclical and can instead be carried out in a non-repetitive configuration, for example, to observe a single reaction or phenomenon such as real time polymerase chain reaction (rtPCR), quantitative PCR (qPCR), binding assays such as detection of epitopes using labeled antibodies, enzyme assays, nucleic acid hybridization assays, array-based genotyping and RNA expression assays and the like.

Particularly useful sequencing reactions are Sequencing By Binding™ (SBB™) reactions such as those described in commonly owned US Pat. App. Pub. Nos. 2017/0022553 A1; 2018/0044727 A1; 2018/0187245 A1; or 2018/0208983 A1, each of which is incorporated herein by reference. Generally, methods for determining the sequence of a template nucleic acid molecule can be based on formation of a ternary complex (between polymerase, primed nucleic acid and cognate nucleotide) under specified conditions. The method can include an examination phase followed by a nucleotide incorporation phase.

The examination phase can be carried out in a flow cell that contains at least one template nucleic acid molecule primed with a primer. The reaction mixture can include the primed template nucleic acid, a polymerase and at least one nucleotide type. Interaction of polymerase and a nucleotide with the primed template nucleic acid molecule(s) can be observed under conditions where the nucleotide is not covalently added to the primer(s); and the next base in each template nucleic acid can be identified using the observed interaction of the polymerase and nucleotide with the primed template nucleic acid molecule(s). The interaction between the primed template, polymerase and nucleotide can be detected in a variety of schemes. For example, the nucleotides can contain a detectable label. Each nucleotide can have a distinguishable label with respect to other nucleotides. Alternatively, some or all of the different nucleotide types can have the same label and the nucleotide types can be distinguished based on separate deliveries of different nucleotide types to the flow cell. In some embodiments, the polymerase can be labeled. Polymerases that are associated with different nucleotide types can have unique labels that distinguish the type of nucleotide to which they are associated. Alternatively, polymerases can have similar labels and the different nucleotide types can be distinguished based on separate deliveries of different nucleotide types to the flow cell. Detection can be carried out by scanning the flow cell using an apparatus or method set forth herein.

During the examination phase, discrimination between correct and incorrect nucleotides can be facilitated by ternary complex stabilization. A variety of conditions and reagents can be useful. For example, the primer can contain a reversible blocking moiety that prevents covalent attachment of nucleotide; and/or cofactors that are required for extension, such as divalent metal ions, can be absent; and/or inhibitory divalent cations that inhibit polymerase-based primer extension can be present; and/or the polymerase that is present in the examination phase can have a chemical modification and/or mutation that inhibits primer extension; and/or the nucleotides can have chemical modifications that inhibit incorporation, such as 5' modifications that remove or alter the native triphosphate moiety.

The extension phase can then be carried out by creating conditions in the flow cell where a nucleotide can be added to the primer on each template nucleic acid molecule. In some embodiments, this involves removal of reagents used in the examination phase and replacing them with reagents that facilitate extension. For example, examination reagents can be replaced with a polymerase and nucleotide(s) that are capable of extension. Alternatively, one or more reagents can be added to the examination phase reaction to create extension conditions. For example, catalytic divalent cations can be added to an examination mixture that was deficient in the cations, and/or polymerase inhibitors can be removed or disabled, and/or extension competent nucleotides can be added, and/or a deblocking reagent can be added to render primer(s) extension competent, and/or extension competent polymerase can be added.

It will be understood that any of a variety of nucleic acid sequencing reactions can be carried out using an apparatus and method of the present disclosure. Other exemplary sequencing methods are set forth below.

Sequencing-by-synthesis (SBS) techniques can be used. SBS generally involves the enzymatic extension of a nascent primer through the iterative addition of nucleotides against a template strand to which the primer is hybridized. Briefly, SBS can be initiated by contacting target nucleic acids, attached to sites in a flow cell, with one or more labeled nucleotides, DNA polymerase, etc. Those sites where a primer is extended using the target nucleic acid as template will incorporate a labeled nucleotide that can be detected. Detection can include scanning using an apparatus or method set forth herein. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can be performed n times to extend the primer by n nucleotides, thereby detecting a sequence of length n. Exemplary SBS procedures, reagents and detection components that can be readily adapted for use with a method or apparatus of the present disclosure are described, for example, in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference. Also useful are SBS methods that are commercially available from Illumina, Inc. (San Diego, Calif.).

Some SBS embodiments include detection of a proton released upon incorporation of a nucleotide into an extension product. For example, sequencing based on detection of released protons can use reagents and an electrical detector that are commercially available from ThermoFisher (Waltham, Mass.) or described in US Pat. App. Pub. Nos. 2009/0026082 A1; 2009/0127589 A1; 2010/0137143 A1; or 2010/0282617 A1, each of which is incorporated herein by reference.

Other sequencing procedures can be used, such as pyrosequencing Pyrosequencing detects the release of inorganic pyrophosphate (PPi) as nucleotides are incorporated into a nascent primer hybridized to a template nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system that is configured to scan a flow cell using apparatus and methods set forth herein.

Sequencing-by-ligation reactions are also useful including, for example, those described in Shendure et al. *Science* 309:1728-1732 (2005); U.S. Pat. No. 5,599,675; or U.S. Pat. No. 5,750,341, each of which is incorporated herein by reference. Some embodiments can include sequencing-by-hybridization procedures as described, for example, in Bains et al., *Journal of Theoretical Biology* 135 (3), 303-7 (1988); Drmanac et al., *Nature Biotechnology* 16, 54-58 (1998); Fodor et al., *Science* 251 (4995), 767-773 (1995); or WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template, for example, using an apparatus or method set forth herein.

Some embodiments can utilize methods involving real-time monitoring of DNA polymerase activity. For example, nucleotide incorporations can be detected through fluorescence resonance energy transfer (FRET) interactions between a fluorophore-bearing polymerase and gamma-phosphate-labeled nucleotides, or with zero-mode waveguides (ZMW). Techniques and reagents for sequencing via detection of fluorescence resonance energy transfer (FRET) and/or detection via zero-mode waveguides (ZMW) can be modified for use in an apparatus or method set forth herein are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008); or U.S. Pat. Nos. 7,315,019; 8,252,911 or 8,530,164, the disclosures of which are incorporated herein by reference.

Steps for the above sequencing methods can be carried out cyclically. For example, examination and extension steps of an SBB™ method can be repeated such that in each cycle a single next correct nucleotide is examined (i.e. the next correct nucleotide being a nucleotide that correctly binds to the nucleotide in a template nucleic acid that is located immediately 5' of the base in the template that is hybridized to the 3'-end of the hybridized primer) and, subsequently, a single next correct nucleotide is added to the primer. Any number of cycles of a sequencing method set forth herein can be carried out including, for example, at least 1, 2, 5, 10, 20, 25, 30, 40, 50, 75, 100, 150 or more cycles. Alternatively or additionally, no more than 150, 100, 75, 50, 40, 30, 25, 20, 10, 5, 2 or 1 cycles are carried out.

Nucleic acid template(s), to be sequenced, can be added to a flow cell using any of a variety of known methods. In some embodiments, a single nucleic acid molecule is to be sequenced. The nucleic acid molecule can be delivered to a flow cell and can optionally be attached to a surface in a flow cell or other vessel. Optionally, the molecule is subjected to single molecule sequencing. Alternatively, multiple copies of the nucleic acid can be made, and the resulting ensemble can be sequenced. For example, the nucleic acid can be amplified on a surface (e.g. on the inner wall of a flow cell) using techniques set forth in further detail below.

A variety of different nucleic acid molecules (i.e. a population having a variety of different sequences) can be sequenced. The molecules can optionally be attached to a surface in a flow cell or other vessel. The nucleic acids can be attached at unique sites on the surface and single nucleic acid molecules that are spatially distinguishable one from the other can be sequenced in parallel. Alternatively, the nucleic acids can be amplified on the surface to produce a plurality of surface attached ensembles. The ensembles can be spatially distinguishable, one ensemble from another ensemble, and sequenced in parallel.

A method set forth herein can use any of a variety of amplification techniques in a flow cell. Exemplary techniques that can be used include, but are not limited to, polymerase chain reaction (PCR), rolling circle amplification (RCA), multiple displacement amplification (MDA), bridge amplification, or random prime amplification (RPA). In particular embodiments, one or more primers used for amplification can be attached to a surface in a flow cell. In such embodiments, extension of the surface-attached primers along template nucleic acids will result in copies of the templates being attached to the surface. Methods that result in one or more sites on a solid support, where each site is attached to multiple copies of a particular nucleic acid template, can be referred to as "clustering" methods.

In PCR embodiments, one or both primers used for amplification can be attached to a surface. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. Nos. 5,641,658 or 7,115,400; U.S. Patent Pub. Nos. 2002/0055100 A1, 2004/0096853 A1, 2004/0002090 A1, 2007/0128624 A1 or 2008/0009420 A1, each of which is incorporated herein by reference. PCR amplification can also be carried out with one of the amplification primers attached to the surface and the second primer in solution. An exemplary format that uses a combination of one solid phase-attached primer and a solution phase primer is known as primer walking and can be carried out as described in U.S. Pat. No. 9,476,080, which is incorporated herein by reference. Another example is emulsion PCR which can be carried out as described, for example, in Dressman et al., *Proc. Natl. Acad. Sci. USA* 100:8817-8822 (2003), WO 05/010145, or U.S. Patent Pub. Nos. 2005/0130173 A1 or 2005/0064460 A1, each of which is incorporated herein by reference.

RCA techniques can be used in a method set forth herein. Exemplary reagents that can be used in an RCA reaction and principles by which RCA produces amplicons are described, for example, in Lizardi et al., *Nat. Genet.* 19:225-232 (1998) or US Pat. App. Pub. No. 2007/0099208 A1, each of which is incorporated herein by reference. Primers used for RCA can be in solution or attached to a surface in a flow cell.

MDA techniques can also be used in a method of the present disclosure. Some reagents and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); or U.S. Pat. Nos. 5,455,166; 5,130,238; or 6,214,587, each of which is incorporated herein by reference. Primers used for MDA can be in solution or attached to a surface in a flow cell.

Nucleic acid templates that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Thus, a mixture of nucleic acids used herein can be derived from a biological source, synthetic source or amplification product. Primers used herein can be DNA, RNA or analogs thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Nucleic acids can also be derived from a prokaryote such as a bacterium, *Escherichia coli, staphylococci* or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference. Cells, tissues, biological fluids, proteins and other samples can be obtained from these organisms and detected using an apparatus or method set forth herein.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. Nos. 6,355,431 or 9,045,796, each of which is incorporated herein by reference. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

An apparatus or method of the present disclosure can employ a polymerase. The polymerase can be stored in a reservoir, flowed through a fluid delivery channel where it can optionally be heated or chilled and provided to a flow cell for a nucleic acid sequencing reaction or other analytical process. Any of a variety of polymerases can be used in a method set forth herein. Reference to a particular polymerase, such as those exemplified throughout this disclosure, will be understood to include functional variants thereof unless indicated otherwise. Particularly useful functions of a polymerase include formation of a ternary complex or catalysis of the polymerization of a nucleic acid strand using an existing nucleic acid as a template. Polymerases can be classified based on structural homology such as the classification of polymerases into families identified as A, B, C, D, X, Y, and RT. DNA Polymerases in Family A include, for example, T7 DNA polymerase, eukaryotic mitochondrial DNA Polymerase γ, *E. coli* DNA Pol I, *Thermus aquaticus* Pol I, and *Bacillus stearothermophilus* Pol I. DNA Polymerases in Family B include, for example, eukaryotic DNA polymerases α, δ, and ε; DNA polymerase ζ; T4 DNA polymerase; Phi29 DNA polymerase; and RB69 bacteriophage DNA polymerase. Family C includes, for example, the *E. coli* DNA Polymerase III alpha subunit. Family B archaeon DNA polymerases include, for example, Vent, Deep Vent, Pfu and 9° N (e.g., Therminator™ DNA polymerase from New England BioLabs Inc.; Ipswich, Mass.) polymerases. Family D includes, for example, polymerases derived from the *Euryarchaeota* subdomain of *Archaea*. DNA Polymerases in Family X include, for example, eukaryotic polymerases Pol β, pot σ, Pol λ, and Pol μ, and *S. cerevisiae* Pol4. DNA Polymerases in Family Y include, for example, Pol η, Pol τ, Pol κ, *E. coli* Pol IV (DINB) and *E. coli* Pol V (UmuD'2C). The RT (reverse transcriptase) family of DNA polymerases includes, for example, retrovirus reverse transcriptases and eukaryotic telomerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and *Archaea* RNA polymerase.

Further examples of useful DNA polymerases include bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, Clostridium stercorarium (Cst) DNA polymerase, Clostridium thermocellum (Cth) DNA polymerase and Sulfolobus solfataricus (Sso) DNA polymerase. Eukaryotic DNA polymerases include DNA polymerases α, β, γ, δ, €, η, ζ, λ, σ, μ, and k, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cp1 DNA polymerase, Cp1 DNA polymerase, T7 DNA polymerase, and T4 polymerase. Other useful DNA polymerases include thermostable and/or thermophilic DNA polymerases such as Thermus aquaticus (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator™ DNA polymerase from New England BioLabs Inc.; Ipswich, Mass.) can be used.

Useful RNA polymerases include, but are not limited to, viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V; and Archaea RNA polymerase.

Another useful type of polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some applications of the methods and systems set forth herein. Polymerases that substantially lack 3'-5' proofreading exonuclease activity are also useful in some configurations, for example, in most sequencing systems and methods. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

Polymerases that may be used in a method or composition set forth herein include naturally occurring polymerases and modified variations thereof, including, but not limited to, mutants, recombinants, fusions, genetic modifications, chemical modifications, synthetics, and analogs. Useful polymerases for ternary complex formation and detection are not limited to polymerases that have the ability to catalyze a polymerization reaction. Optionally, a useful polymerase will have the ability to catalyze a polymerization reaction in at least one condition that is not used during formation or examination of a stabilized ternary complex. Exemplary polymerases that can be used to form a stabilized ternary complex include, for example, wild type and mutant polymerases set forth in US Pat. App. Pub. Nos. 2017/0314072 A1 or 2018/0155698 A1, each of which is incorporated herein by reference.

Polymerases that contain an exogenous label moiety (e.g., an exogenous luminophore), which can be used to detect the polymerase, can be useful in some embodiments. Optionally, the exogenous label moiety can be chemically linked to the polymerase, for example, using a free sulfhydryl or a free amine moiety of the polymerase. An exogenous label moiety can also be attached to a polymerase via protein fusion. Exemplary label moieties that can be attached via protein fusion include, for example, green fluorescent protein (GFP), phycobiliprotein (e.g. phycocyanin and phycoerythrin) or wavelength-shifted variants of GFP or phycobiliprotein.

An apparatus or method of the present disclosure can employ a nucleotide. The nucleotide can be stored in a reservoir, flowed through a fluid delivery channel where it can optionally be heated or chilled and provided to a flow cell for a nucleic acid sequencing reaction or other analytical process. The nucleotide can be a native nucleotide, nucleotide analog or modified nucleotide as desired to suit a particular application or configuration of the methods. Such nucleotides can be present in a ternary complex or used in a sequencing method set forth herein.

Optionally, a nucleotide analog has a nitrogenous base, five-carbon sugar, and phosphate group, wherein any moiety of the nucleotide may be modified, removed and/or replaced as compared to a native nucleotide. Nucleotide analogs may be non-incorporable nucleotides (i.e. nucleotides that are incapable of reacting with the 3' oxygen of a primer to form a covalent linkage). Such nucleotides that are incapable of incorporation include, for example, monophosphate and diphosphate nucleotides. In another example, the nucleotide may contain modification(s) to the triphosphate group that render the nucleotide non-incorporable. Examples of non-incorporable nucleotides may be found in U.S. Pat. No. 7,482,120, which is incorporated by reference herein. In some embodiments, non-incorporable nucleotides may be subsequently modified to become incorporable. Non-incorporable nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, or caged nucleotides. Further examples of nucleotide analogs are described in U.S. Pat. No. 8,071,755, which is incorporated by reference herein.

Nucleotide analogs that are used in a method or system herein can include terminators that reversibly prevent subsequent nucleotide incorporation at the 3'-end of the primer after the analog has been incorporated into the primer. For example, U.S. Pat. Nos. 7,544,794 and 8,034,923 (the disclosures of these patents are incorporated herein by reference) describe reversible terminators in which the 3'-OH group is replaced by a 3'-ONH$_2$ moiety. Another type of reversible terminator is linked to the nitrogenous base of a nucleotide as set forth, for example, in U.S. Pat. No. 8,808,989 (the disclosure of which is incorporated herein by reference). Other reversible terminators that similarly can be used in connection with the methods described herein include those described in references cited elsewhere herein or in U.S. Pat. Nos. 7,956,171, 8,071,755, and 9,399,798 (the disclosures of these U.S. patents are incorporated herein by reference). For example, an —O-azidomethyl moiety is particularly useful as a reversible terminator when present at the 3' position of a nucleotide. In certain embodiments, a reversible terminator moiety can be removed from a primer, in a process known as "deblocking," allowing for subsequent nucleotide incorporation. Compositions and methods for deblocking are set forth in references cited herein in the context of reversible terminators.

Alternatively, nucleotide analogs irreversibly prevent nucleotide incorporation at the 3'-end of the primer to which they have been incorporated. Irreversible nucleotide analogs include 2',3'-dideoxynucleotides (ddNTPs such as ddGTP, ddATP, ddTTP, ddCTP). Dideoxynucleotides lack the 3'-OH group of dNTPs that would otherwise participate in polymerase-mediated primer extension. Thus, the 3' position has a hydrogen moiety instead of the native hydroxyl moiety. Irreversibly terminated nucleotides can be particularly useful for genotyping applications or other applications where primer extension or sequential detection along a template nucleic acid is not desired.

Nucleotide analogs that are used herein, for example, to participate in stabilized ternary complexes, neednot include blocking groups (e.g. reversible terminators) that prevent subsequent nucleotide incorporation at the 3'-end of the primer after the analog has been incorporated into the primer. This can be the case whether or not an extension step is carried out using nucleotide(s) having a blocking group (e.g. reversible terminator). It will be understood that a blocking group can be present on a nucleotide analog that participates in a stabilized ternary complex, if desired.

A nucleotide that is used herein, for example, to participate in forming a stabilized ternary complex, can include an exogenous label. An exogenously labeled nucleotide can include a reversible or irreversible terminator moiety, an exogenously labeled nucleotide can be non-incorporable, an exogenously labeled nucleotide can lack terminator moieties, an exogenously labeled nucleotide can be incorporable or an exogenously labeled nucleotide can be both incorporable and non-terminated. Exogenously labeled nucleotides can be particularly useful when used to form a stabilized ternary complex with a non-labeled polymerase.

Alternatively, a nucleotide that is used herein, for example, to participate in forming a ternary complex can lack exogenous labels (i.e. the nucleotide can be "non-labeled"). A non-labeled nucleotide can include a reversible or irreversible terminator moiety, a non-labeled nucleotide can be non-incorporable, a non-labeled nucleotide can lack terminator moieties, a non-labeled nucleotide can be incorporable, or a non-labeled nucleotide can be both incorporable and non-terminated. Non-labeled nucleotides can be useful when a label on a polymerase is used to detect a stabilized ternary complex or when label-free detection is used. Non-labeled nucleotides can also be useful in an extension step of a method set forth herein. It will be understood that absence of a moiety or function for a nucleotide refers to the nucleotide having no such function or moiety. However, it will also be understood that one or more of the functions or moieties set forth herein for a nucleotide, or analog thereof, or otherwise known in the art for a nucleotide, or analog thereof, can be specifically omitted in a method or composition set forth herein.

Optionally, a nucleotide (e.g. a native nucleotide or nucleotide analog) is present in a mixture during or after formation of a stabilized ternary complex. For example, at least 1, 2, 3, 4 or more nucleotide types can be present. Alternatively or additionally, at most 4, 3, 2, or 1 nucleotide types can be present. Similarly, one or more nucleotide types that are present can be complementary to at least 1, 2, 3 or 4 base types in a template nucleic acid. Alternatively or additionally, one or more nucleotide types that are present can be complementary to at most 4, 3, 2, or 1 base types in a template nucleic acid. Different base types can be identifiable by the presence of different exogenous labels on the different nucleotides. Alternatively, two or more nucleotide types can have exogenous labels that are not distinguishable. In the latter format the different nucleotides can nevertheless be distinguished due to being separately delivered to a reaction vessel or due to an encoding and decoding scheme as set forth, for example, in US Pat. App. Pub. No. 2018/0305749 A1 or U.S. Pat. No. 9,951,385, each of which is incorporated herein by reference.

Systems and methods of the present disclosure can employ detectable labels on reactants or products that are to be detected. In many cases the labels are exogenous labels added to a reactant or product, such as a polymerase, nucleic acid or nucleotide. Examples of useful exogenous labels include, but are not limited to, radiolabel moieties, luminophore moieties, fluorophore moieties, quantum dot moieties, chromophore moieties, enzyme moieties, electromagnetic spin labeled moieties, nanoparticle light scattering moieties, and any of a variety of other signal generating moieties known in the art. Suitable enzyme moieties include, for example, horseradish peroxidase, alkaline phosphatase, beta-galactosidase, or acetylcholinesterase. Exemplary fluorophore labels include, but are not limited to rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones;

eosin; erythrosin; Malachite green; CY dyes (GE Biosciences), including Cy3 (and its derivatives) and Cy5 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (boron-dipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610, ATTO 635; ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED, EPOCH YAKIMA YELLOW, EPOCH GIG HARBOR GREEN; Tokyo green (M. Kamiya, et al., 2005 *Angew. Chem. Int. Ed.* 44:5439-5441); and CF dyes including CF 647 and CF555 (Biotium), and others known in the art such as those described in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland.

A label can be attached to a nucleotide, polymerase or other molecule via a linker. A linker that is present in a nucleotide or polymerase can be, but need not be, cleavable. For example, the linker can be stable to conditions used in methods set forth herein such that the covalent structure of the linker is not changed during any particular step, or throughout all steps, of a method set forth herein.

A reactant or product can lack exogenous labels. For example, a stabilized ternary complex and all components participating in the stabilized ternary complex (e.g. polymerase, template nucleic acid, primer and/or cognate nucleotide) can lack one, several, or all of the exogenous labels described herein or in the references that are cited and incorporated herein. In such embodiments, ternary complexes can be detected based on intrinsic properties of the stabilized ternary complex, such as mass, charge, intrinsic optical properties or the like. Exemplary methods for detecting non-labeled ternary complexes are set forth in commonly owned U.S. Pat. App. Pub. No. 2017/0022553 A1 PCT App. Ser. No. PCT/US16/68916, or U.S. Pat. App. Ser. Nos. 62/375,379 or 15/677,870, each of which is incorporated herein by reference.

An apparatus or method of the present disclosure can further include a chiller for drawing heat from a fluid delivery channel or from a flow cell. The chiller(s) can be present (or used) in addition to the heaters set forth herein. For example, a chiller can be used in combination with a heater to allow temperature regulation in two directions. The chiller can be used to reduce the temperature of a fluid in a delivery channel, detection channel, rotary valve or other fluidic component, and the heater can be used to increase the temperature of such fluidic components. Some configurations can use a thermal transfer device that is capable of functioning as a heat source and heat sink such as a Peltier device. Alternatively, the chiller(s) can be present (or used) instead whereby one or more of the heaters set forth herein is replaced with a chiller. A chiller can be positioned in an apparatus as exemplified for heaters, with the exception that modifications can be made to accommodate the different temperature effects.

Accordingly, the present disclosure provides an apparatus for performing an analytical procedure such as determining the sequence of a nucleic acid. The apparatus can include (a) a stage configured to support a flow cell; (b) a detector configured to observe a detection channel of the flow cell when the flow cell is supported by the stage; (c) a plurality of fluid delivery channels, wherein each of the fluid delivery channels fluidically connects a reservoir to the detection channel of the flow cell; and (d) a first chiller configured to chill the plurality of fluid delivery channels. Optionally, the stage comprises a second chiller that is configured to chill a flow cell that is supported by the stage. Optionally, the apparatus can include a thermostat configured to detect the temperature of a fluid delivery channel in the plurality of fluid delivery channels and to selectively activate the first heater and the first chiller. As a further option, the apparatus can include a second chiller configured to chill the flow cell that is supported by the stage. The apparatus can also include a thermostat configured to detect the temperature of the flow cell and to selectively activate the second heater and the second chiller.

This disclosure further provides a method for performing an analytical procedure such as determining the sequence of a nucleic acid. The method can include steps of (a) providing an analytical apparatus having a flow cell, a fluidic system and a detection system, wherein the flow cell contains an array of analytes, such as nucleic acids, in a detection channel, wherein the fluidic system includes a fluid delivery channel that fluidically connects a reservoir to the detection channel of the flow cell, wherein the detection system observes signals from the array of analytes; (b) transferring a liquid reagent from the reservoir to a chilled region of the fluid delivery channel, whereby the liquid reagent is chilled; (c) contacting the chilled liquid reagent with the array of analytes by transferring the chilled liquid reagent to the detection channel; and (d) detecting signals from the array of analytes via the detection system. In nucleic acid sequencing configurations, the liquid reagent is a reagent used for sequencing nucleic acids.

Methods and apparatus for preheating fluid reagents can be used in combination with methods and apparatus for delivering mixed phase fluids (e.g. a fluid foam, fluid slurry or fluid emulsion) to a flow cell such as those set forth in U.S. patent application Ser. No. 16/700,422, which claims priority to U.S. patent application Ser. No. 62/774,998, each of which is incorporated herein by reference. A mixed phase fluid apparatus or method, such as those set forth in U.S. patent application Ser. No. 62/774,998 can be modified using apparatus or methods set forth herein to heat the mixed phase fluid prior to delivery to a flow cell. Conversely, a heating apparatus or method set forth herein can be modified to produce a mixed phase fluid using apparatus or methods set forth in U.S. patent application Ser. No. 16/700,422 or U.S. patent application Ser. No. 62/774,998.

EXAMPLE I

Thermal Model for a Nucleic Acid Sequencing System

This Example presents a thermal model showing the benefit of preheating fluid reagents for use in a Sequencing By Binding™ (SBB™) system. The SBB™ system is configured for optical detection of fluorescently labeled ternary complexes formed on an array of primed nucleic acids in a glass flow cell. A ternary complex consists of a polymerase, one of the primed template nucleic acids and a next correct nucleotide for the primed template nucleic acid.

Figure 2:
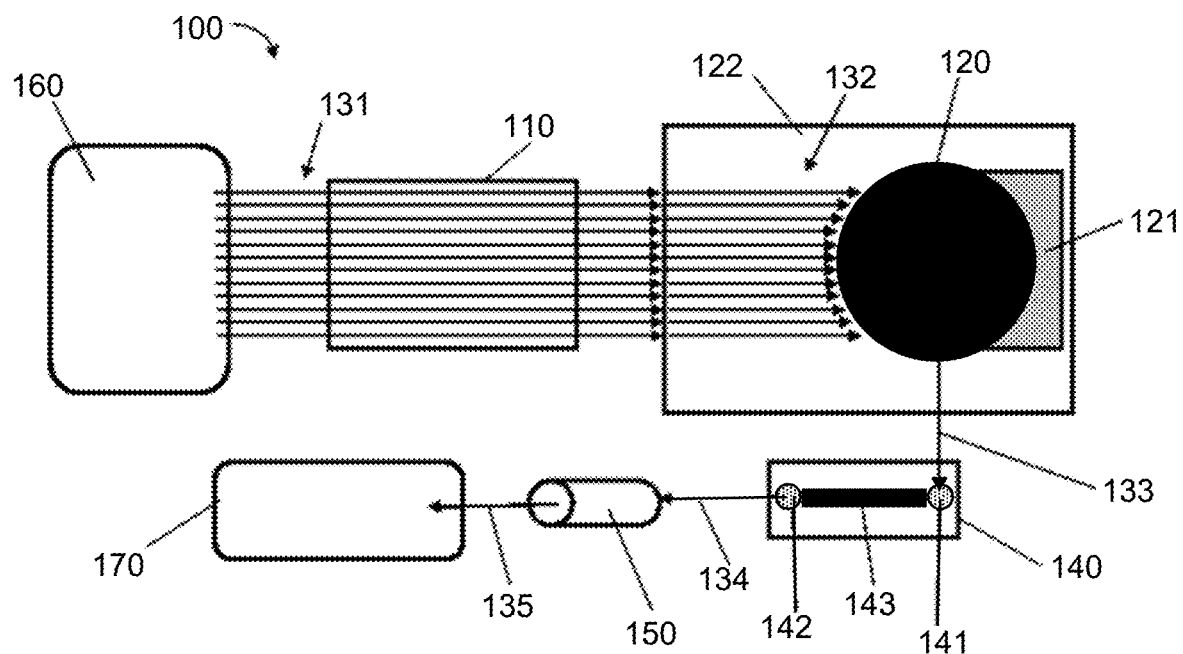
FIG. 2 shows a block diagram of an exemplary nucleic acid sequencing system.

A block diagram of an exemplary sequencing system 100 is shown in FIG. 2. Sequencing reagents are stored at room temperature or chilled in a reagent pack 160. Fluid reagents from each reservoir in the pack are transferred via fluid delivery channels 131 passing through a preheater 110 to manifold 122. Manifold fluid delivery channels 132 transfer the preheated fluids to rotary valve 120 which is heated by heater 121. Rotary valve 120 is used to select reagents from manifold fluid delivery channels 132 for delivery to flow cell 140 via common fluid delivery channel 133. The common fluid delivery channel 133 is fluidically connected to detection channel 143 via ingress port 141 and the fluids exit the detection channel 143 via egress port 142. Syringe pump 150, which typically contain a selector valve, pulls fluids from reagent pack 160 through the flow cell 140 and through channels 134 and 135 to waste reservoir 170.

A 1-layer thermal model was constructed. The 1-layer model assumes that the flow cell starts at the established temperature and that fluid (water) has not begun to be warmed by the flow cell. The model assumes infinite thermal capacity for the flow cell and provides an understanding of the impact of having a temperature differential between the fluid and the flow cell into which it is injected. Relevant characteristics for the materials used in the model are shown in Table 1. Characteristics calculated from these characteristics are shown in Table 2. The volume of water with an equivalent thermal mass to the surface of the flow cell was calculated to be 95 µl.

TABLE 1

| Material | k (W/(m * K)) | Thickness (m) | Heat Capacity (J/(Kg)) | Density (Kg/m$^3$) |
| --- | --- | --- | --- | --- |
| Air | 0.02 | $1 \times 10^{-4}$ | 1 | 1.225 |
| Glass | 1.5 | $1 \times 10^{-3}$ | 0.7 | 2700 |
| Water | 0.6 | $1.25 \times 10^{-4}$ | 4.18 | 1000 |

TABLE 2

| Material | Thermal Mass per Area (J/(Kg * m$^2$)) | Conductance per Area (W/K) | Thermal Mass (J/K) | Resistivity (K/W) | Fraction of Thermal Resistance |
| --- | --- | --- | --- | --- | --- |
| Air | $1.23 \times 10^{-1}$ | $2 \times 10^2$ | $2.57 \times 10^{-5}$ | $5 \times 10^{-3}$ | 0.85 |
| Glass | $1.89 \times 10^3$ | $1.5 \times 10^3$ | $3.97 \times 10^{-1}$ | $6.67 \times 10^{-4}$ | 0.11 |
| Water | $5.23 \times 10^2$ | $4.8 \times 10^3$ | $1.1 \times 10^{-1}$ | $2.08 \times 10^{-4}$ | 0.04 |

Figure 3:
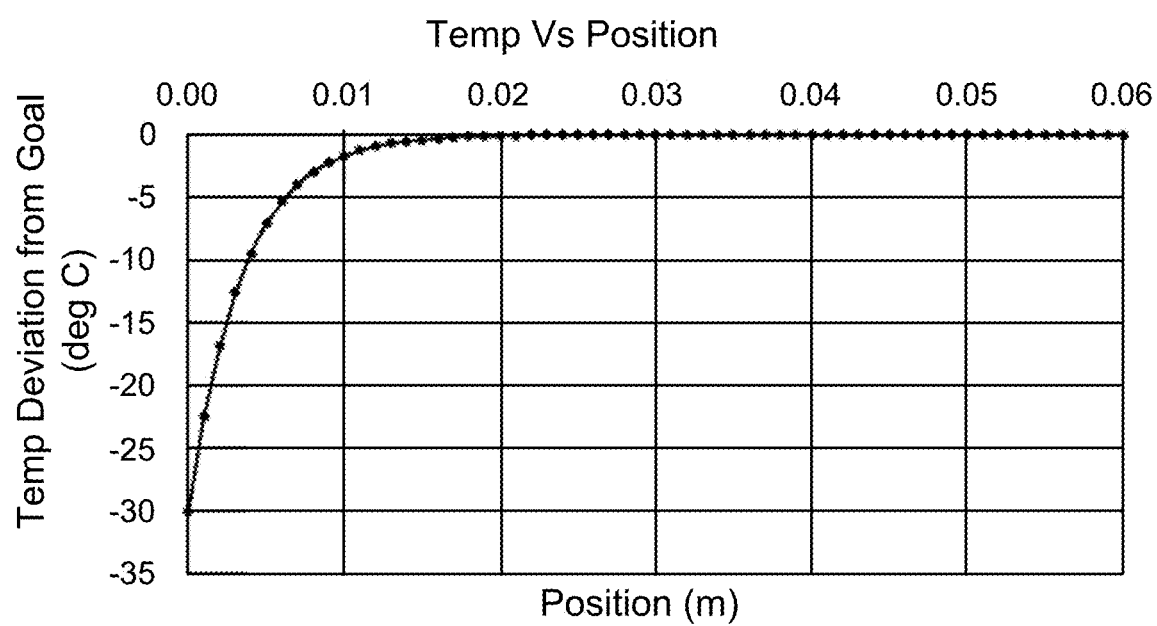
FIG. 3 shows a plot of water temperature vs. position in a flow cell based on a 1-layer thermal model.

FIG. 3 shows a plot of water temperature vs. position in a flow cell based on a 1-layer model. The results of the model indicate how long it takes for water to warm up as it flows through a flow cell assuming that the flow cell is up to temperature when the flow happens and that the flow cell is not cooled by a cold reagent. As is evident from the plot of the 1-layer model, an array in the flow cell would be subject to a temperature gradient across the first 2 cm of the flow cell. This could have an adverse impact for a temperature sensitive reaction.

Figure 4:
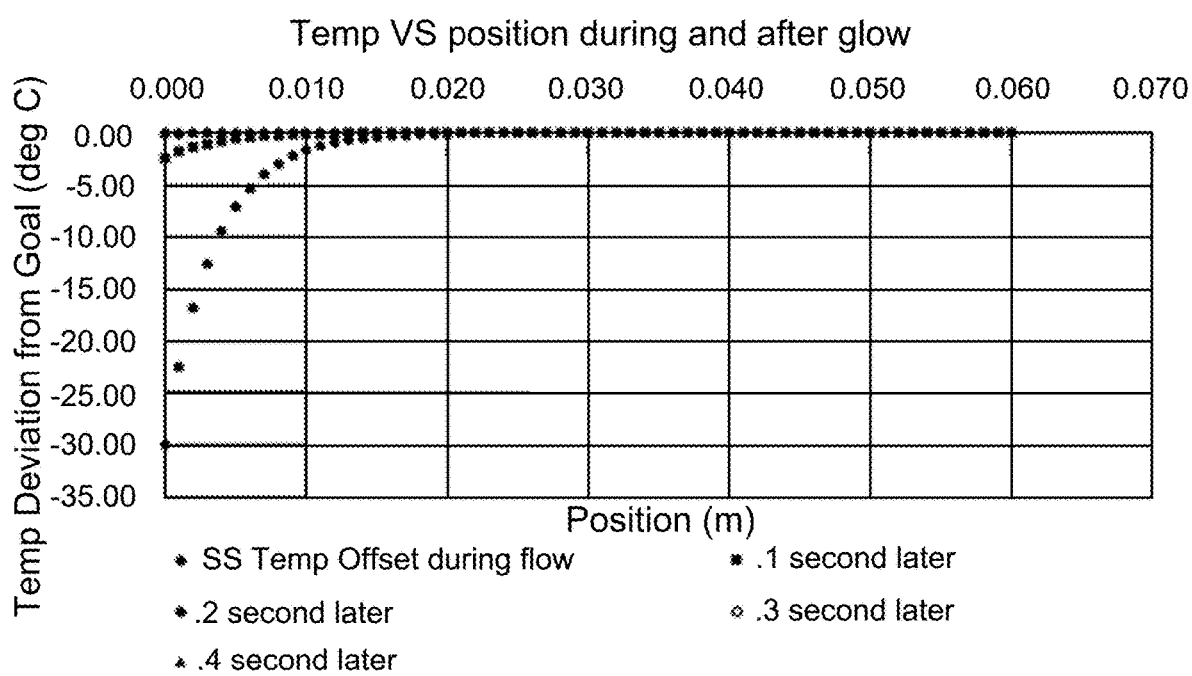
FIG. 4 shows plots of water temperature vs position in a flow cell at various timepoints during and after initiating flow of water in the flow cell based on the 1-layer thermal model.

FIG. 4 shows plots of water temperature vs position in the flow cell at various timepoints during and after initiating flow of water in the flow cell based on the 1-layer model.

Water is a good proxy for sequencing reagents which are generally provided in aqueous fluids. The water equilibrates to the temperature of the flow cell by about 0.2 seconds according to the 1-layer model. The 1-layer model is accurate on a short time scale (e.g. early in the flow directly after a thorough incubation).

Figure 5:
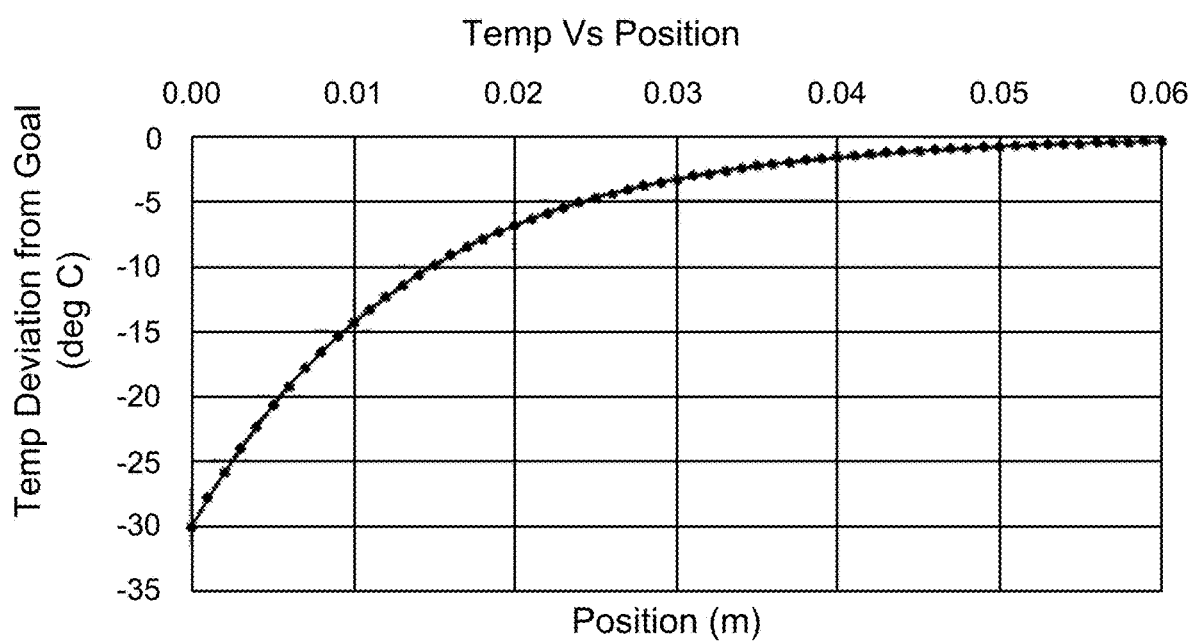
FIG. 5 shows a plot of water temperature vs. position in a flow cell based on a 3-layer thermal model.

A 3-layer thermal model was used to evaluate heat transfer thorough the glass at steady state during flow of water. FIG. 5 shows a plot of water temperature vs. position in a flow cell based on the 3-layer model. This model assumes that the flow and thermal profile are in a steady state and then shows the theoretical thermal recovery after stopping flow. By neglecting the thermal capacity of the glass, the thermal recovery profile is a better case scenario than when considering the thermal energy needed to warm the glass as the fluid warms. As is evident from the plot of the 3-layer model, an array in the flow cell would be subject to a temperature gradient across the first 6 cm of the flow cell.

Figure 6:
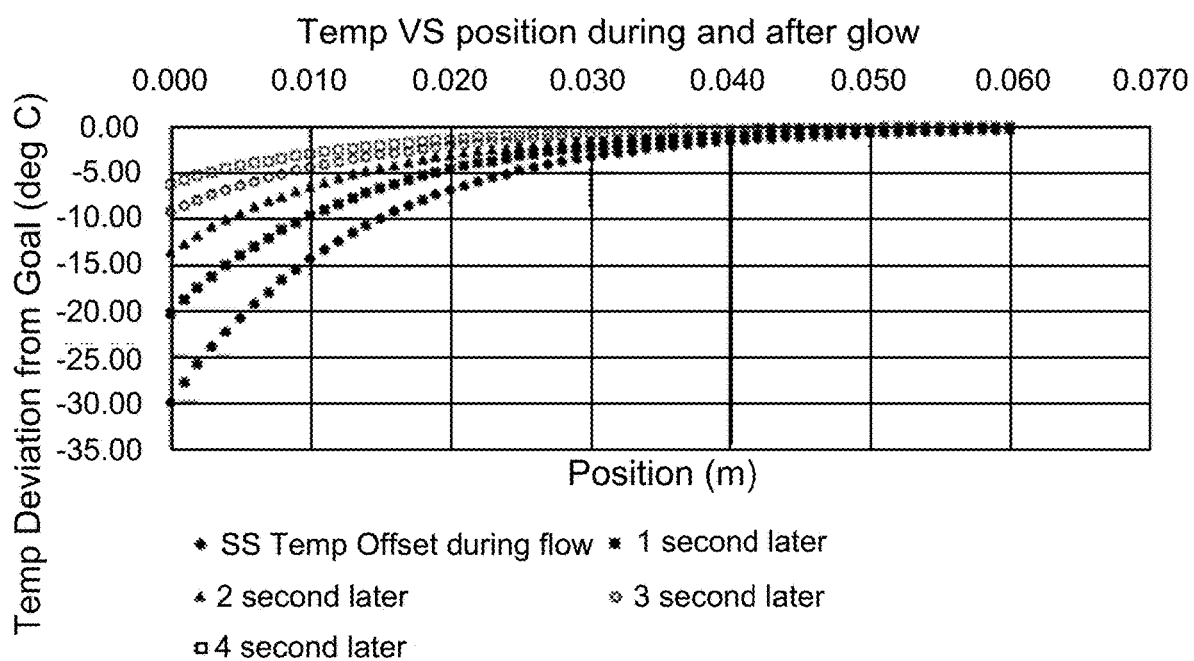
FIG. 6 shows plots of water temperature vs position in the flow cell at various timepoints during and after initiating flow of water in the flow cell based on the 3-layer thermal model.

FIG. 6 shows plots of water temperature vs position in the flow cell at various timepoints during and after initiating flow of water in the flow cell based on the 3-layer model. The water does not fully equilibrate to the temperature of the flow cell within the 0.4 second timeframe evaluated under the 3-layer model. The 3-layer model is good for looking at volumes of flow which will have depleted any heat banked in the glass during an incubation. However, this model does not include thermal conduction through the side of the flow cell that is opposite the side that is proximal to the heater.

The results of the model suggest that flows of room temperature aqueous reagents into the flow cell would cause significant cooling of an array within the flow cell (on the order of 10° C. for a flow cell that is maintained at 60° C.). The results further suggest that it can take a significant amount of time to reheat an array in a flow cell (on the order of tens of seconds). The results suggest that preheating aqueous reagents would help improve sequencing results. This preheating may also decrease the time and/or volume of aqueous reagent required to achieve uniform results across an array and over time.

EXAMPLE II

Thermal Testing of Fluidic Delivery Components of a Nucleic Acid Sequencing System This example provides empirical tests to determine the thermal properties of a fluidic delivery system that is used in a nucleic acid sequencing platform.

Figure 7:
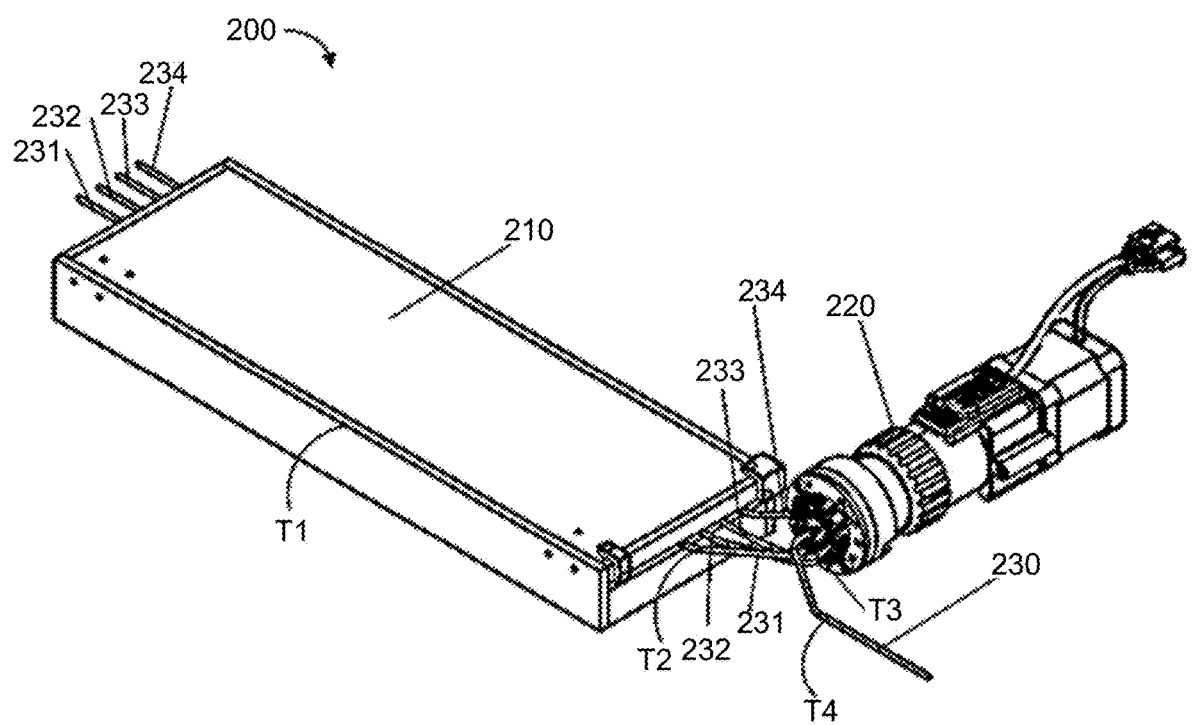
FIG. 7 shows a test rig used for evaluating thermal properties of preheated fluids prior to entering a flow cell.

Tests were performed on test rig 200 shown in FIG. 7. Test rig 200 includes four fluid lines 231 to 234 that pass through preheater 210 and then connect to rotary valve 220. The rotary valve 220 connects the four fluid lines 231 to 234 to common line 230 which in turn is connected to a flow cell (not shown). Thermocouples were used to measure temperature at four locations: T1 detects the middle of preheater 210, T2 detects channel 231 where it exits preheater 210, T3 detects common line 230 about 2 cm from the connection to rotary valve 220, and T4 detects common line 230 about 10 cm from the connection to rotary valve 220. K type thermocouples were used but can be replaced with J type thermocouples.

The preheater 210 and rotary valve 220 had a set point of 60° C. Water was at a temperature of 20-22° C. prior to entering the rig under a positive pressure of 15 PSI. All channels were made from silicone tubing and had dimensions of 0.031" inner diameter, 5/32" outer diameter (0.787 mm ID/3.968 mm OD). Measurements were taken from each thermocouple at 1 second intervals.

Figure 8B:
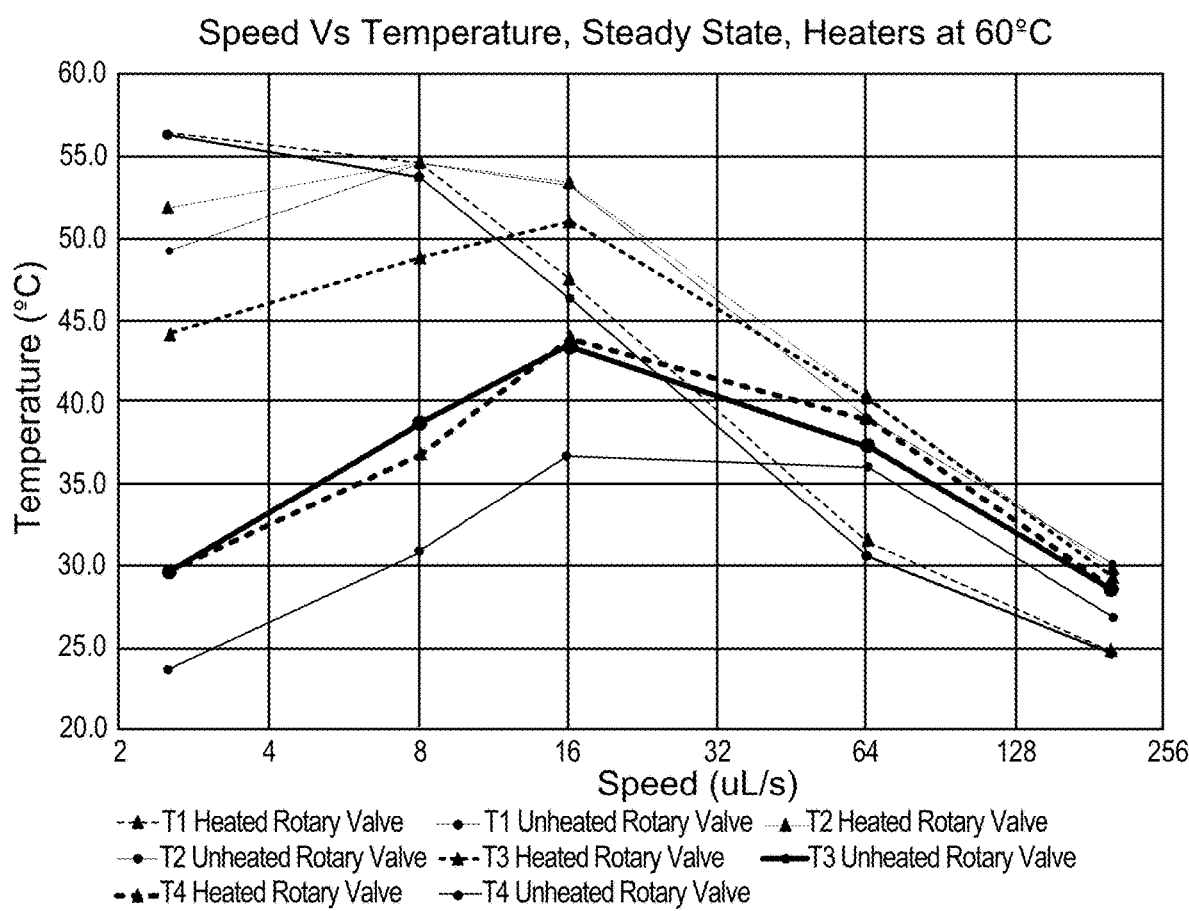
FIG. 8B shows plots of results obtained from evaluation of thermal properties of fluids prior to entry into a flow cell.

Tabular results obtained from test rig 200 are shown in FIG. 8A and the same results are plotted in FIG. 8B. The data was collected from a single fluid delivery channel of the test rig 200. The results demonstrate the impact of heating the rotary valve downstream of the preheater and its effects on the T3 and T4 temperature in a steady state condition. The results indicate that setting the pre-heater to a temperature of 60° C. allows fluidic reagents to be delivered to the flow cell at a temperature of about 44° C. The data shows that the incubating fluid in the preheater (allowing fluid to come up to temperature) is counteracted by the heat transfer in the fluid delivery channels to the ambient environment.

Figure 9:
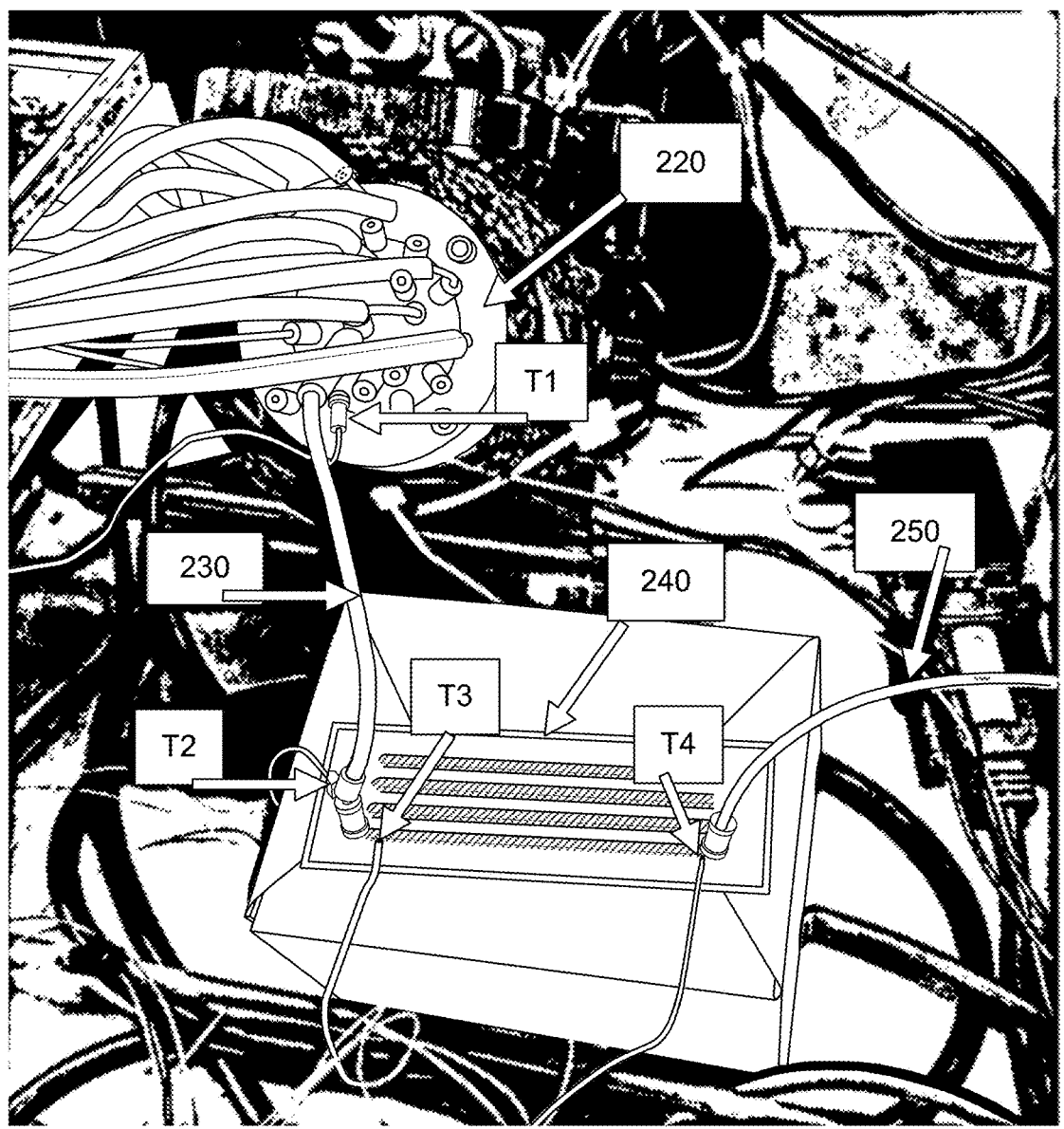
FIG. 9 shows a test rig used for evaluating thermal properties of preheated fluids while flowing through a flow cell.

The test rig was used to detect temperatures at different locations downstream of the valve. The test rig was modified to reposition the thermocouples as shown in FIG. 9. Specifically, T1 was placed to detect the common line 230 at the point of exit from the heated rotary valve 220, T2 was placed at the connector to the ingress for flow cell 240, T3 was placed at the ingress for flow cell 240, and T4 was placed at the egress for flow cell 240 near the common line 250 leaving the flow cell. This test rig included 12 fluidic delivery channels all pulling 20-22° C. distilled water and flowed 160 uL of liquid at the flow rates displayed on the x-axis per pulse.

Figure 10B:
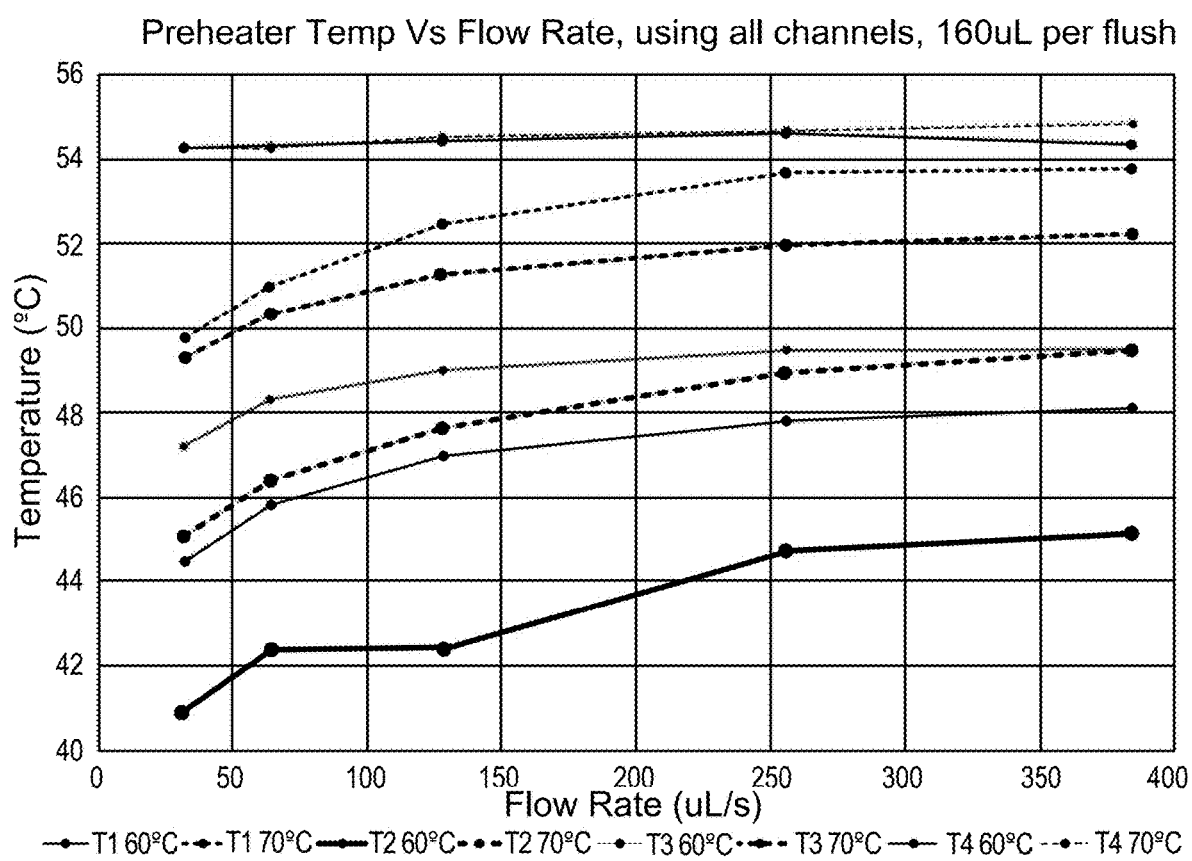
FIG. 10B shows plots of results obtained from evaluation of thermal properties of fluids flowing through a flow cell.

Tabular results obtained from the modified test rig are shown in FIG. 10A and the same results are plotted in FIG. 10B. The data was collected using fluid flows through twelve fluid delivery channels of the test rig 200. The results assume that each reagent has come up to temperature after 1 minute in the preheater (in accordance with the results from FIG. 8, which suggest that after about 20 seconds reagents heat up to 60° C. in the preheater). The results show the difference in setpoints (60° C. vs 70° C.) as well as showing that when operating at fast flow rates, there is a decrease in heat loss, likely because less heat is lost to the ambient air in the lines. Insulting the fluid delivery channels between the preheater and flow cell can be done to further reduce the heat loss.

EXAMPLE III

Nucleic acid Sequencing Apparatus

This example describes an apparatus for sequencing nucleic acids, the apparatus including (a) a stage in contact with a flow cell, wherein the flow cell comprises at least one detection channel, wherein the detection channel comprises an array of nucleic acids; (b) a detector configured to observe the array of nucleic acids in the detection channel; (c) a plurality of reservoirs containing reagents for sequencing the array of nucleic acids; (d) a plurality of fluid delivery channels, wherein the fluid delivery channels fluidically connect the plurality of reservoirs to the detection channel of the flow cell; (e) a first heater that transfers heat to the plurality of fluid delivery channels; and (f) a second heater that transfers heat to the detection channel of the flow cell.

Several of the components and functions of the nucleic acid sequencing system are set forth in further detail below. It will be understood that the system is exemplary. One or more of the components set forth below can be omitted or replaced with other components, for example, as set forth elsewhere herein. Other components that are set forth herein can be added to the exemplary system without necessarily replacing a component exemplified below.

Figure 11:
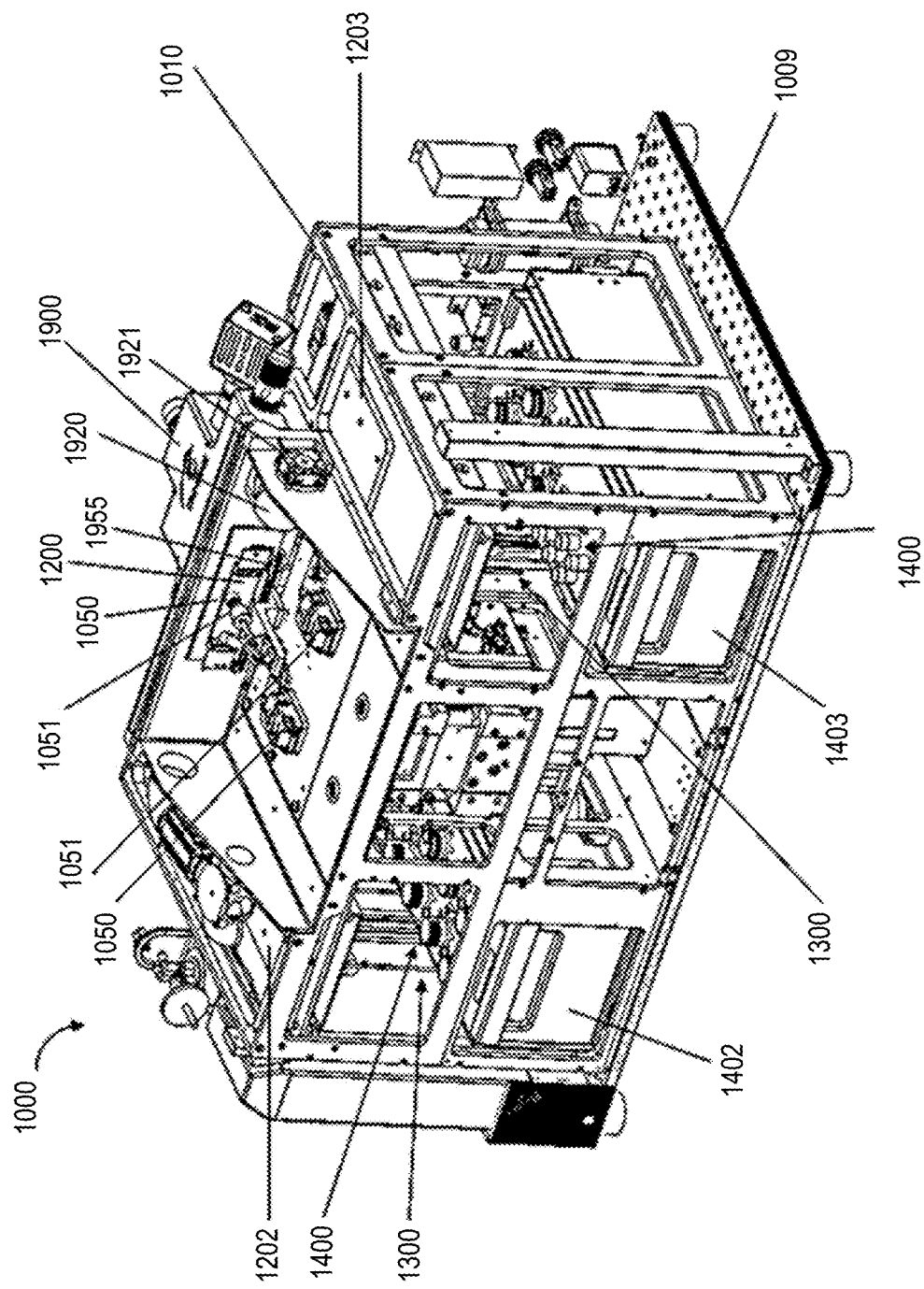
FIG. 11 shows a perspective view of an assembly of several components of a nucleic acid sequencing apparatus.

FIG. 11 shows a perspective view of an assembly of several components of nucleic acid sequencing apparatus 1000. Apparatus 1000 is supported by base 1009 and frame 1010. The top middle region of frame 1010 is configured for a user to access the system in order to place flow cell 1200 on heated stage 1950. Stage 1950 provides a conductive surface for transferring heat from a heating element to flow cell 1200. The stage includes a reference surface that makes direct contact with a region of the flow cell surface, such that heat is conducted to the region of the flow cell that is in contact with the heated reference surface. Other regions of the flow cell are not in direct contact with the stage and are instead heated by transfer from a surface of the stage, through an air gap to the flow cell surface. Flow cell 1200 is pressed to stage 1950 by preload 1951. As such, flow cell 1200 is positioned to be detected by optical detector 1900. Flow cell 1200 is translated along stage 1950 by translational components 1955 and held to a reference surface on stage 1950 to allow detection of an array of nucleic acids (or other analytical sample) inside flow cell 1200. Components and operation of preload 1951, scanning system 1955 and optical detector 1900 are set forth in US Pat. App. Pub. No. 2019/0055596 A1, which is incorporated herein by reference. The system also includes vent pipe 1920 and fan 1921 for removing heat generated by the optical detector.

In the view of FIG. 11, fluidic connections between routing manifold 1500 and flow cell 1200 have been removed and are instead shown in FIG. 14. The plurality of reservoirs 1400 is shown in FIG. 11 as the reservoirs are engaged by sipper array 1300. Also shown are drawers 1402 and 1403 which allow the user to replace liquids in the reservoirs. The reservoirs can be filled with reagents for a nucleic acid sequencing process. Exemplary reagents include, but are not limited to polymerases, nucleotides and other reagents set forth elsewhere herein, or in references cited herein, in the context of nucleic acid sequencing. Optionally, the nucleotides and/or polymerases can be exogenously labeled for example with luminophores, such as those set forth herein or in references cited herein. Also visible in FIG. 11 are conduction heater 1202 and conduction heater 1203, which are positioned to heat sipper manifolds as set forth below.

FIG. 11 also shows nucleic acid sequencing apparatus 1000 further includes peristaltic pumps 1050 and 1051 which are configured to apply fluid displacement forces (e.g. positive pressure, positive displacement or the like) at a location in the fluid delivery component that is between plurality of reservoirs 1400 and instrument connectors (FIGS. 14A and 14B) thereby delivering fluid from the fluid delivery component to flow cell 1200. In exemplary apparatus 1000, the pumps can be configured to apply fluid displacement forces to the fluid delivery component at a location that is between the rotary valve and the instrument connector component, thereby delivering fluid from the fluid delivery component to the flow cell.

Figure 12:
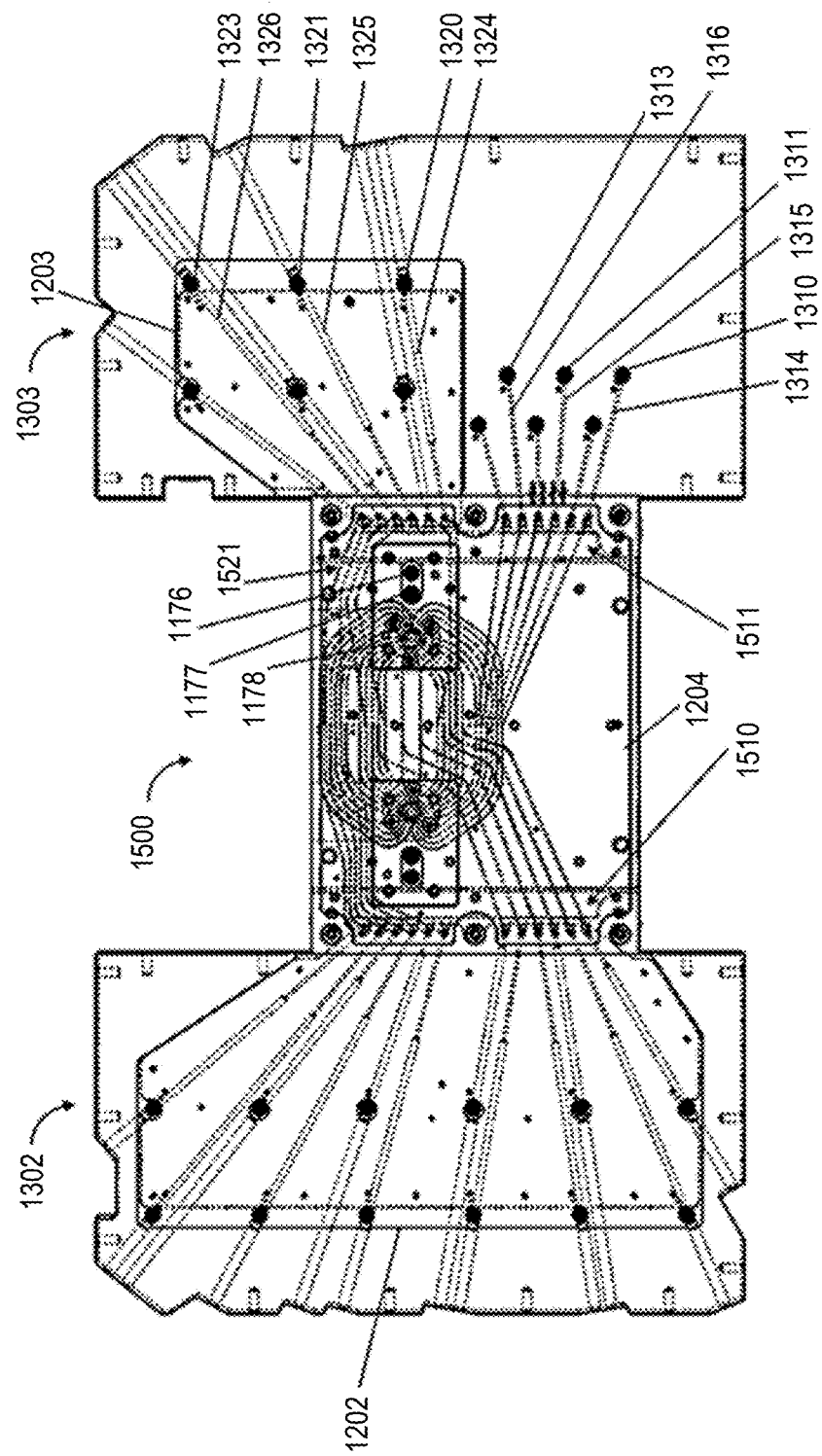
FIG. 12 shows a top view of a routing manifold, sipper arrays, rotary valves and conduction heaters.

FIG. 12 shows a top view of routing manifold 1500 fluidically connected to sipper manifold 1302 and sipper manifold 1303. The manifolds are composed of polyetherimide)(Ultem®). Sippers attach to the sipper manifolds such that liquid drawn from a reservoir by the sipper is transferred through the sipper manifold to routing manifold 1500 by dedicated channels. For example, sipper manifold 1303 includes sipper attachment points 1320, 1321 and 1323 which are fluidically connected to fluid lines 1324, 1325 and 1326, respectively, within sipper manifold 1303. Fluidic lines 1324, 1325 and 1326 are heated by conduction heater 1203. Fluid lines 1324, 1325 and 1326 connect to respective lines in routing manifold 1500 via fluidic lines 1521 to deliver the reagents to rotary valve 1560 (see FIG. 13). Fluidic lines 1521 are heated by conduction heater 1204. Thus, fluid that is drawn from reservoirs via sipper attachment points 1320, 1321 and 1323 are heated by conduction heaters 1203 and 1204 in route to rotary valve 1560. Conduction heaters 1202, 1203 and 1204 are polyimide heaters (also known as Kapton heaters) having silicone insulators.

Sipper manifold 1303 also includes sipper attachment points 1310, 1311 and 1313 which are fluidically connected to fluid lines 1314, 1315 and 1316, respectively, within sipper manifold 1303. Fluid lines 1314, 1315 and 1316 are not in direct contact with a conduction heater. Fluid lines 1314, 1315 and 1316 connect to respective lines in routing manifold 1500 via connections 1511 to deliver the reagents to rotary valve 1560. Fluidic lines 1511 are heated by conduction heater 1204. The fluidic lines are channels drilled in the Ultem™ block. As such, the bulk of the block is heated and the walls of the channels transfer heat to the fluids within. FIG. 12 also shows connections 1510, on routing manifold 1500, which connect to respective connections on sipper manifold 1302 such that fluid drawn through the sippers can be directed to rotary valve 1550. All the sipper attachment points and fluidic lines in sipper manifold 1302 are heated by contact with conduction heater 1202.

Figure 13:
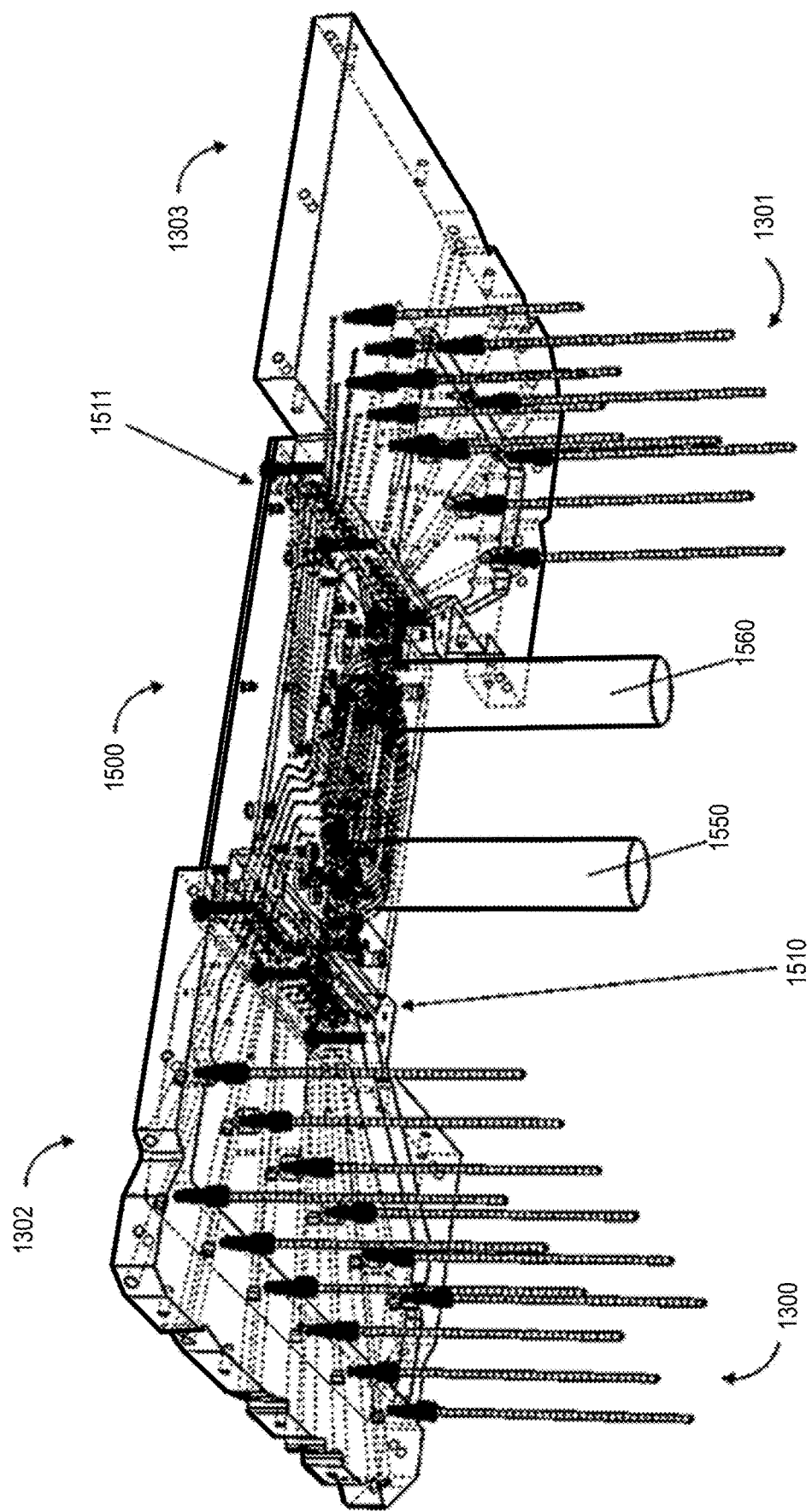
FIG. 13 shows a bottom view of a routing manifold, sipper arrays, rotary valves and conduction heaters.

Rotary valves 1550 and 1560 are visible in FIG. 13 which shows a bottom view of routing manifold 1500. Also visible in FIG. 13 are sipper array 1300 and sipper array 1301, which include sippers that attach to sipper manifold 1302 and sipper manifold 1303, respectively. FIG. 12 also shows egress port 1178 which connects the outflow of rotary valve 1560 (FIG. 13) to instrument connector 1110, fluidic ingress port 1176 which connects the egress of flow cell 1200 to a waste tank, and optional gas egress port 1177 which delivers gas from a compressed air source to instrument connector 1110 (FIGS. 14A and 14B). Similar fluidic ports are present for rotary valve 1550. Gas egress port 1177 can be utilized when a bubble generator is used to introduce bubbles into liquid reagents from the reservoirs. The resulting foam can be delivered to the flow cell to provide a variety of advantages such as reduced reagent consumption per volume of flow cell used and more rapid exchange of different reagents, when compared to non-foam liquids. Exemplary bubble generators, other hardware and methods for using foam to sequence nucleic acids and to perform other analytical procedures are set forth in U.S. patent application Ser. No. 16/700,422, which is incorporated herein by reference. For example, in particular configurations a bubble generator can be housed within instrument connector 1110 (FIGS. 14A and 14B).

FIG. 14A shows a perspective view of the fluidic connection between nucleic acid sequencing system 1000 (FIG. 11) and flow cell 1200. FIG. 14B shows the same perspective, but with the connectors disconnected and slightly displaced. Instrument connector 1110 engages with instrument connection port 1172. Instrument connection port 1172 contains fluid ingress 1176 (FIG. 14B), liquid egress 1178 (FIG. 14B) and optional gas egress port 1177 (FIG. 14B). Instrument connector 1110 is fluidically connected to flow cell connector 1180 by flexible tubes 1191 and 1192. Flow cell connector 1180 engages with flow cell port 1190. Flow cell connector 1180 provides a fluid ingress for a first detection channel in flow cell 1200 and a fluid egress for a second detection channel in flow cell 1200. Instrument connector 1110 is configured to fluidically connect flexible tube 1191 to a channel ingress of the flow cell and to connect flexible tube 1192 to a channel egress of the flow cell. Instrument connector 1110 can be engaged with instrument connection port 1172 by hand since the connector 1110 has compressible hook 1120 (FIG. 14B), which fits a complementary latch. Similarly, flow cell connector 1180 can be engaged with flow cell connection port 1190 by hand since connector 1180 has compressible hooks that fit complementary latches. Note that a second connection can be made from instrument connection port 1141 to flow cell port 1140 using connectors that are similar to those exemplified for instrument connection port 1172 to flow cell port 1190. The second connection can include a fluid ingress for the second detection channel in flow cell 1200 and a fluid egress for the first detection channel in flow cell 1200. As such fluid will flow through the two detection channels of flow cell 1200 in opposite directions.

Also shown in FIGS. 14A and 14B are peristaltic pumps 1050 and 1051. FIGS. 14A and 14B show peristaltic pump 1050 has a rotor that contacts flexible tube 1193 to apply positive pressure upstream of instrument connector 1110. Flexible tube 1193 passes from hole 1130 (FIG. 14A) of instrument connector 1110, then over the rotor of peristaltic pump 1050, and then into hole 1131 (FIG. 14A) of instrument connector 1110. Also shown is preload 1950 which pushes flow cell 1200 to contact a reference surface on stage 1950. When flow cell 1200 is pushed to stage 1950, the flow cell is aligned with detection optics 1900 (FIG. 11) and the flow cell is heated by heat transfer from the surface of stage 1950.

Figure 15:
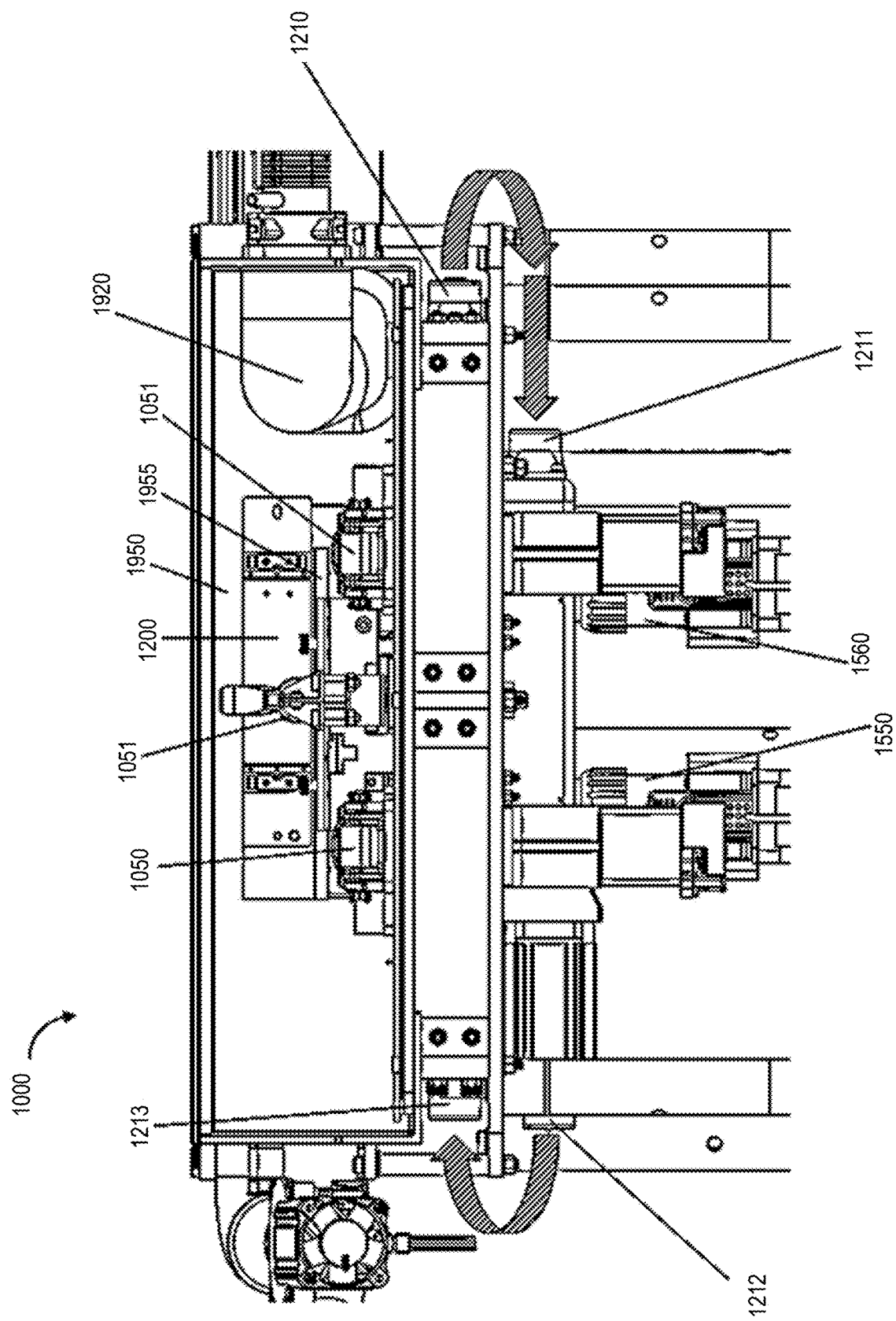
FIG. 15 shows a front view of sequencing apparatus 1000 and includes hatched arrows indicating the direction of heat conduction.

FIG. 15 shows a front view of sequencing apparatus 1000 and includes hatched arrows indicating the direction of hot air circulation. Warm air from a heating element is transferred via convection out egress 1210 and circulates to enter ingress 1211. The heat convection warms rotary valves 1560 and 1550 and passes out egress 1212. The heat then circulates into ingress 1213. The heat convection provides an optional means to heat the fluidic components as an alternative or addition to the conduction heaters shown in FIGS. 11 through 13. FIG. 15 also shows peristaltic pumps 1050 and 1051, flow cell 1200, stage 1950, preload 1951, scanning system 1955, and vent pipe 1920.

As demonstrated by this example, a nucleic acid sequencing apparatus can include three heated spaces, the first space being fluidic delivery channels that are heated by conduction and/or convection, the second space being air space around various fluidic components such as connectors, fluid delivery channels and the flow cell, and the third space being the flow cell stage which is heated by direct contact with a reference surface on the stage and by proximity to other surfaces on the stage.

Throughout this application various publications, patents and/or patent applications have been referenced. The disclosures of these documents in their entireties are hereby incorporated by reference in this application.

The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

A number of embodiments have been described. Nevertheless, it will be understood that various modifications may be made. Accordingly, other embodiments are within the scope of the following claims.

What is claimed is:

1. A method for sequencing nucleic acids, comprising:
    (a) providing a sequencing apparatus comprising a flow cell, a fluidic system, a delivery channel heater, a flow cell heater and a detection system,
    wherein the flow cell comprises an array of nucleic acids in a detection channel,
    wherein the fluidic system comprises a fluid delivery channel that fluidically connects a reservoir to the detection channel of the flow cell,
    wherein the detection system observes signals from the array of nucleic acids;
    (b) performing two or more sequencing cycles comprising the steps of:
        (i) transferring a fluidic sequencing reagent from the reservoir to a heated region of the fluid delivery channel;
        (ii) delivering heat from the delivery channel heater to the fluidic sequencing reagent while the fluidic sequencing reagent is at rest in the heated region, whereby the fluidic sequencing reagent is heated;
        (iii) contacting the heated fluidic sequencing reagent with the array of nucleic acids by transferring the heated fluidic sequencing reagent from the heated region to the detection channel; and
        (iv) delivering heat from the flow cell heater to the sequencing reagent in the detection channel, wherein the delivery channel heater has the same set point as the flow cell heater; and
    (c) detecting signals from the array of nucleic acids via the detection system during the cycles;
    thereby sequencing the nucleic acids.

2. The method of claim 1, wherein the fluid delivery channel is at a higher temperature than the reservoir.

3. The method of claim 2, wherein the flow cell is at a higher temperature than the reservoir.

4. The method of claim 1, wherein the flow cell heater delivers heat to the flow cell by conduction.

5. The method of claim 1, wherein the delivery channel heater delivers heat to the fluid delivery channel by conduction.

6. The method of claim 1, wherein the sequencing apparatus further comprises a convection heater that transfers heat to the fluid delivery channel.

7. The method of claim 6, wherein the convection heater is set to a temperature that is higher than the reservoir.

8. The method of claim 1, wherein the volume of the detection channel is at most 10 ml.

9. The method of claim 1, wherein the volume of the detection channel is at most 1 ml.

10. The method of claim 1, wherein the sequencing apparatus further comprises a valve configured to control the flow of fluidic sequencing reagent through the fluid delivery channel.

11. The method of claim 10, wherein the valve comprises a rotary valve.

12. The method of claim 11, wherein the sequencing apparatus further comprises a heater configured to heat the valve.

13. The method of claim 1, wherein the array comprises at least $1 \times 10^3$ different nucleic acids.

14. The method of claim 13, wherein the nucleic acids are immobilized at sites in the array and wherein the sites each comprise an area of less than 25 square microns.

15. The method of claim 1, wherein the array further comprises a plurality of ternary complexes, wherein each of the ternary complexes comprises a nucleic acid of the array, a polymerase and a next correct nucleotide for the nucleic acid.

16. The method of claim 1, wherein the cross-sectional area of the detection channel is at most 100 $mm^2$.

17. The method of claim 1, wherein the sequencing apparatus further comprises a second reservoir.

18. The method of claim 17, wherein the heated region of the fluid delivery channel fluidically connects the reservoir and the second reservoir to the detection channel of the flow cell.

19. The method of claim 17, wherein a second fluid delivery channel fluidically connects the second reservoir to the detection channel of the flow cell.

20. The method of claim 19, further comprising
    (f) transferring a second fluidic sequencing reagent from the second reservoir to a heated region of the second fluid delivery channel;
    (g) delivering heat from a second delivery channel heater to the second fluidic sequencing reagent while the second fluidic sequencing reagent is at rest in the heated region of the second fluid delivery channel, whereby the second fluidic sequencing reagent is heated;
    (h) contacting the heated second fluidic sequencing reagent with the array of nucleic acids by transferring the heated second fluidic sequencing reagent to the detection channel; and
    (i) delivering heat from the flow cell heater to the second sequencing reagent in the detection channel and detecting signals from the array of nucleic acids via the detection system.

21. The method of claim 1, wherein the heated region of the fluidic delivery channel comprises at least 90% of the volume of the detection channel.

22. The method of claim 1, wherein the set point of the flow cell heater is at most 80° C.

23. The method of claim 1, wherein the set point of the delivery channel heater is at most 80° C.

* * * * *